United States Patent
Kamon

(10) Patent No.: US 12,303,097 B2
(45) Date of Patent: May 20, 2025

(54) MEDICAL IMAGE PROCESSING APPARATUS, ENDOSCOPE SYSTEM, AND MEDICAL IMAGE PROCESSING METHOD

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/670,271

(22) Filed: May 21, 2024

(65) Prior Publication Data
US 2024/0298873 A1    Sep. 12, 2024

Related U.S. Application Data

(63) Continuation of application No. 17/373,908, filed on Jul. 13, 2021, now Pat. No. 12,035,879, which is a
(Continued)

(30) Foreign Application Priority Data

Feb. 8, 2019    (JP) ................................. 2019-021803

(51) Int. Cl.
*A61B 1/00*    (2006.01)
*G06T 7/00*    (2017.01)
(Continued)

(52) U.S. Cl.
CPC .... *A61B 1/000094* (2022.02); *A61B 1/00045* (2013.01); *G06T 7/0012* (2013.01);
(Continued)

(58) Field of Classification Search
CPC .......... A61B 1/000094; A61B 1/00045; A61B 1/000096; A61B 1/0669; A61B 1/07;
(Continued)

(56) References Cited

U.S. PATENT DOCUMENTS 9,788,709 B2 * 10/2017 Yamaguchi .......... A61B 1/0051
10,945,807 B2   3/2021 Gibby et al.
(Continued)

FOREIGN PATENT DOCUMENTS

EP    3603483 A1    2/2020
JP    H04-34671 A    2/1992
(Continued)

OTHER PUBLICATIONS

An Office Action mailed by China National Intellectual Property Administration on Jul. 4, 2024, which corresponds to Chinese Patent Application No. 202080012641.2 and is related to U.S. Appl. No. 18/670,271; with English language translation.
(Continued)

*Primary Examiner* — Juan A Torres
(74) *Attorney, Agent, or Firm* — Studebaker Brackett PLLC

(57) ABSTRACT

A medical image processing apparatus including a processor configured to acquire a medical image from a medical apparatus that sequentially captures images of a plurality of areas in a living body of a subject, acquire area information indicating an area in the living body in the acquired medical image, perform recognition on the medical image as a recognizer; and cause a display apparatus to display a result of the recognition in a mode suitable for the area indicated by the area information.

16 Claims, 15 Drawing Sheets

Related U.S. Application Data continuation of application No. PCT/JP2020/003093, filed on Jan. 29, 2020.

(51) Int. Cl.
  *A61B 1/06* (2006.01)
  *A61B 1/07* (2006.01)

(52) U.S. Cl.
  CPC ....... *A61B 1/000096* (2022.02); *A61B 1/0669* (2013.01); *A61B 1/07* (2013.01); *G06T 2207/10068* (2013.01); *G06T 2207/20081* (2013.01); *G06T 2207/20104* (2013.01)

(58) Field of Classification Search
  CPC ..... A61B 1/0005; A61B 1/045; G06T 7/0012; G06T 2207/10068; G06T 2207/20081; G06T 2207/20104
  USPC ......................................................... 348/68
  See application file for complete search history.

(56) References Cited

U.S. PATENT DOCUMENTS

| | | | |
|---|---|---|---|
| 2011/0001811 A1 | 1/2011 | Imade | |
| 2012/0327205 A1 | 12/2012 | Takahashi | |
| 2014/0028821 A1 | 1/2014 | Tanaka et al. | |
| 2017/0374292 A1* | 12/2017 | Motoki | H04N 23/635 |
| 2018/0144453 A1* | 5/2018 | Koiso | A61B 1/045 |
| 2018/0242817 A1 | 8/2018 | Imaizumi et al. | |
| 2019/0082929 A1* | 3/2019 | Watanabe | A61B 1/0655 |
| 2020/0069160 A1 | 3/2020 | Oosake | |
| 2020/0279368 A1 | 9/2020 | Tada et al. | |

FOREIGN PATENT DOCUMENTS

| | | |
|---|---|---|
| JP | H08-224209 A | 9/1996 |
| JP | H10-69517 A | 3/1998 |
| JP | 2004-265125 A | 9/2004 |
| JP | 2011-135983 A | 7/2011 |
| JP | 2011-156203 A | 8/2011 |
| JP | 2012-249956 A | 12/2012 |
| JP | 2017-012676 A | 1/2017 |
| WO | 2009-104340 A1 | 8/2009 |
| WO | 2013-140667 A1 | 9/2013 |
| WO | 2017/073338 A1 | 5/2017 |
| WO | 2018/179991 A1 | 10/2018 |
| WO | 2018/221033 A1 | 12/2018 |
| WO | 2018/225448 A1 | 12/2018 |

OTHER PUBLICATIONS

International Search Report issued in PCT/JP2020/003093; mailed Apr. 7, 2020.

International Preliminary Report on Patentability and Written Opinion issued in PCT/JP2020/003093; issued Aug. 10, 2021.

The extended European search report issued by the European Patent Office on Mar. 3, 2022, which corresponds to European Patent Application No. 20752785.4-1126 and is related to U.S. Appl. No. 17/373,908.

Office Action issued in JP 2020-571119; mailed by the Japanese Patent Office on Aug. 8, 2022.

An Office Action; "Decision of Refusal", mailed by the Japanese Patent Office on Feb. 10, 2023, which corresponds to Japanese Patent Application No. 2020-571119 and is related to U.S. Appl. No. 17/373,908; with English language translation.

An Office Action mailed by China National Intellectual Property Administration on Sep. 22, 2023, which corresponds to Chinese Patent Application No. 202080012641.2 and is related to U.S. Appl. No. 17/373,908; with English language translation.

An Office Action mailed by China National Intellectual Property Administration on Mar. 16, 2024, which corresponds to Chinese Patent Application No. 202080012641.2 and is related to U.S. Appl. No. 17/373,908; with English language translation.

Communication pursuant to Article 94(3) EPC issued by the European Patent Office on Nov. 13, 2024, which corresponds to European Patent Application No. 20 752 785.4-1122 and is related to U.S. Appl. No. 18/670,271.

Nakashima Hirotaka et al., "Artificial intelligence diagnosis of Helicobacter pylori infection using blue laser imaging-bright and linked color imaging: a single-center prospective study", Annals of Gastroenterology, vol. 31, No. 4, May 3, 2018, pp. 462-468.

Park Young Sun et al., "Colonoscopic Polyp Detection using Convolutional Neural Networks", Proceedings of SPIE Medical Imaging 2016: Computer-Aided Diagnosis, vol. 9785, Mar. 24, 2016, pp. 978528-1 to 978528-6.

Iwahori Yuji et al., "Classification and Size & Shape Recovery from Endoscope Image for Supporting Medical Diagnosis", Comprehensive Engineering, vol. 30, Mar. 31, 2018, pp. 18-36.

An Office Action; "Notice of Reasons for Refusal," mailed by the Japanese Patent Office on Jun. 6, 2024, which corresponds to Japanese Patent Application No. 2023-075660; with English language translation.

* cited by examiner

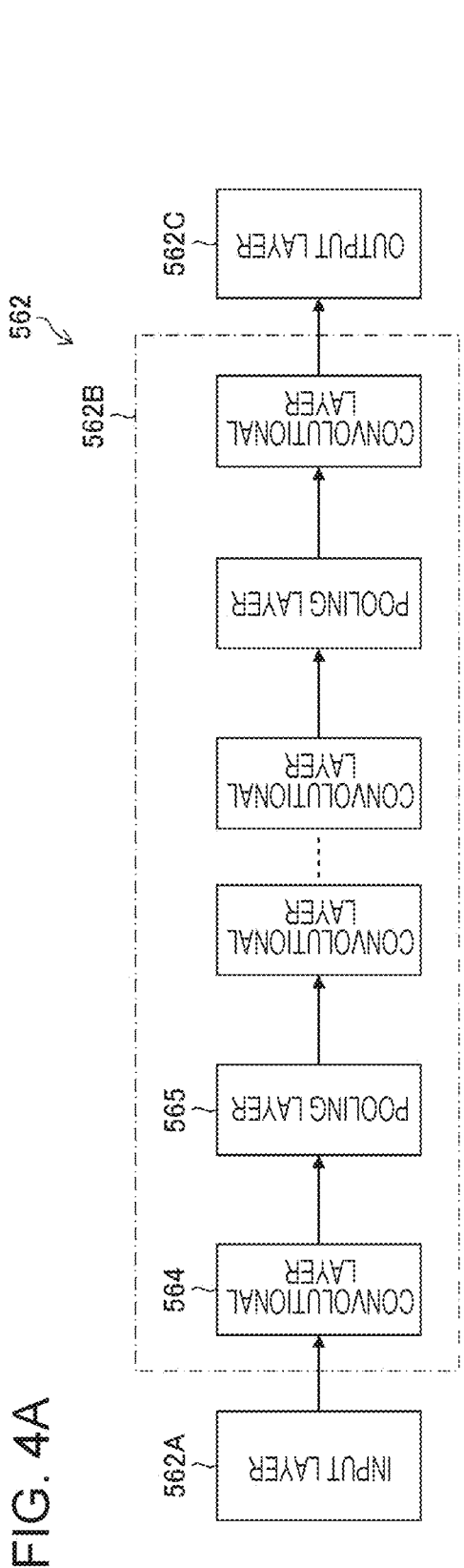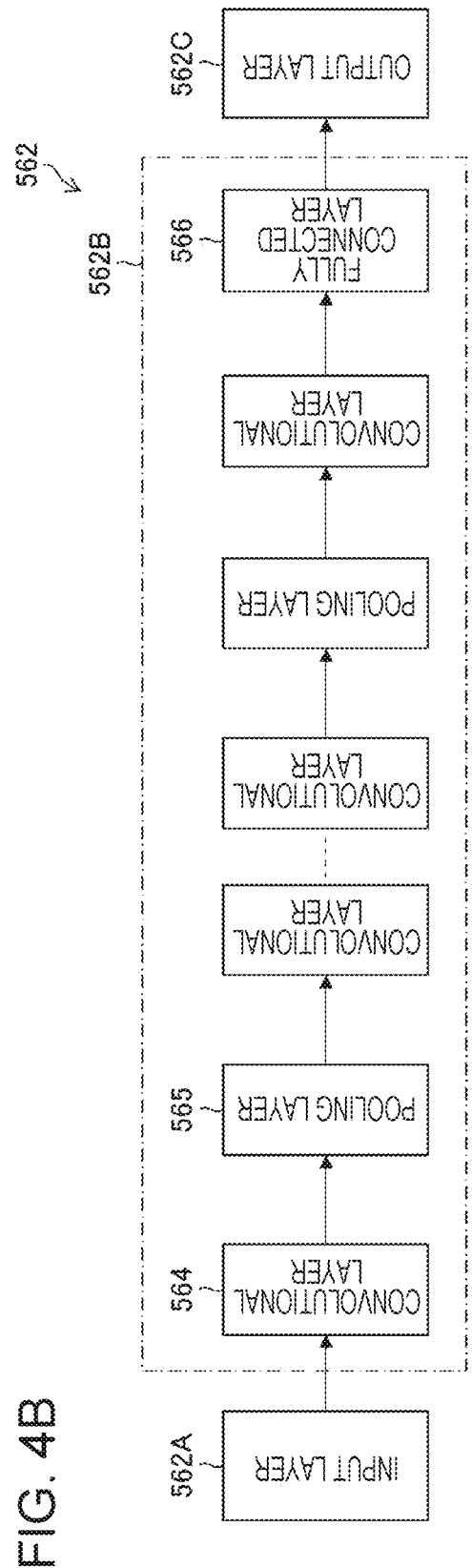

MEDICAL IMAGE PROCESSING APPARATUS, ENDOSCOPE SYSTEM, AND MEDICAL IMAGE PROCESSING METHOD

CROSS-REFERENCE TO RELATED APPLICATIONS

This application is a Continuation of U.S. patent application Ser. No. 17/373,908 filed Jul. 13, 2021, which is a Continuation of PCT International Application No. PCT/JP2020/003093 filed on Jan. 29, 2020, which claims priority under 35 U.S.C § 119(a) to Japanese Patent Application No. 2019-021803 filed on Feb. 8, 2019. Each of the above application(s) is hereby expressly incorporated by reference, in its entirety, into the present application.

BACKGROUND OF THE INVENTION

1. Field of the Invention

The present invention relates to a medical image processing apparatus, an endoscope system, and a medical image processing method that perform recognition on a medical image.

2. Description of the Related Art

Emphasizing an image and changing a display mode have been known as methods for assisting a user, such as a medical doctor, in observing or diagnosing a medical image. For example, JP2011-135983A describes that the type of subject image is determined on the basis of a feature quantity of a narrow-band light image, and emphasis processing is performed on a white-light image on the basis of a result of the determination.

SUMMARY OF THE INVENTION

In the case of observing or diagnosing a medical image, an assistance method needs to be changed because the purpose or method of diagnosis varies according to an area. JP2011-135983A mentioned above describes that a feature quantity calculation method or an emphasis processing method (color conversion) is changed according to whether a target of observation or diagnosis is an upper alimentary canal or a lower alimentary canal, or according to a depth at which blood vessels are present. However, no consideration is given to how to display a recognition result in the case of continuously observing different areas (different organs or different positions in the same organ) during the same examination.

As described above, it is difficult for the existing technique to display a recognition result of a medical image in a manner suitable for an area.

The present invention has been made in view of these circumstances, and it is an object of the present invention to provide a medical image processing apparatus, an endoscope system, and a medical image processing method that are capable of displaying a recognition result of a medical image in a manner suitable for an area.

To achieve the above-described object, a medical image processing apparatus according to a first aspect of the present invention includes a medical image acquiring unit that acquires a medical image from a medical apparatus that sequentially captures images of a plurality of areas in a living body of a subject, an area information acquiring unit that acquires area information indicating an area in the living body in the acquired medical image, a recognizer that performs recognition on the medical image, and a display control unit that causes a display apparatus to display a result of the recognition in a mode suitable for the area indicated by the area information.

The medical image processing apparatus according to the first aspect causes the display apparatus to display a recognition result of a medical image captured for each of a plurality of areas in a mode suitable for the area. Thus, the recognition result of the medical image can be displayed in a manner suitable for the area. In addition, a user is capable of easily grasping switching of the area as a recognition target. Note that the "area" means an organ (esophagus, stomach, small intestine, large intestine, or the like) and/or a difference in position in an organ, and that a case where a distance (depth) from a surface is different at the same position of the same organ is not included in "difference in area".

In the first aspect, "acquisition of a medical image" includes sequential acquisition of a plurality of medical images captured at a determined frame rate. The acquisition may be performed in real time or in non-real time.

The medical image processing apparatus according to the first aspect can be implemented as, for example, a processor of a medical image processing system, but is not limited to such an aspect. The "medical image" is an image acquired as a result of imaging, measurement, or the like performed on a living body, such as a human body, for the purpose of diagnosis, treatment, measurement, or the like, and may be, for example, an endoscopic image, an ultrasound image, a computed tomography (CT) image, or a magnetic resonance imaging (MRI) image. Apparatuses that acquire these images can be used as examples of the "medical apparatus" according to the first aspect.

In a medical image processing apparatus according to a second aspect, in the first aspect, the recognizer includes a plurality of recognizers, each of the plurality of recognizers performing recognition on the medical image and corresponding to one of the plurality of areas in the living body, and a recognizer selected from among the plurality of recognizers in accordance with the area indicated by the area information performs recognition on the medical image. According to the second aspect, the recognizer includes a plurality of recognizers each corresponding to one of the plurality of areas, that is, one of the plurality of areas in the living body. A recognizer selected in accordance with the area indicated by the area information performs recognition on the medical image, and thus recognition suitable for the area can be performed. In the second aspect, "a plurality of recognizers" may include a plurality of recognizers that perform the same type of recognition (detection, classification, measurement, or the like) in methods and/or conditions (items, values, or the like of parameters) suitable for areas, or may include a plurality of recognizers that perform different types of recognition suitable for an area. A plurality of recognizers that are different in type, method, and/or condition may be included. In the second aspect, the medical image processing apparatus is capable of selecting a recognizer in accordance with area information.

In a medical image processing apparatus according to a third aspect, in the first or second aspect, the area information acquiring unit acquires the area information by analyzing the medical image. The third aspect defines one aspect of an area information acquisition method. For example, the area information can be acquired on the basis of a feature quantity of the medical image.

In a medical image processing apparatus according to a fourth aspect, in the first or second aspect, the area information acquiring unit acquires, as the area information, information input by a user. The fourth aspect defines one aspect of an area information acquisition method.

In a medical image processing apparatus according to a fifth aspect, in the first or second aspect, the medical image processing apparatus further includes an area estimating unit that estimates the area by using an external device different from the medical image acquiring unit, and the area information acquiring unit acquires, as the area information, information indicating the estimated area. The fifth aspect defines one aspect of an area information acquisition method, and it is possible to use a device that estimates an area by using a magnetic wave, an ultrasonic wave, or the like.

In a medical image processing apparatus according to a sixth aspect, in any one of the first to fifth aspects, the recognizer is a learned model. Preferably, the learned model is a model that has learned by using an image set constituted by captured images of a living body.

In a medical image processing apparatus according to a seventh aspect, in any one of the first to sixth aspects, the display control unit causes the display apparatus to display information in a display mode suitable for the area such that the information is superimposed on the medical image. In the seventh aspect, characters, numerals, figures, symbols, and a combination thereof are included in examples of the "information". The information to be display and/or the color or brightness thereof may vary according to a recognition result and/or the certainty of a recognition result.

In a medical image processing apparatus according to an eighth aspect, in any one of the first to seventh aspects, the display control unit performs control to display or hide the result of the recognition in accordance with the area. Accordingly, a recognition result of a medical image can be displayed in a manner suitable for the area, and the user is capable of efficiently observing the recognition result in a manner suitable for the area.

In a medical image processing apparatus according to a ninth aspect, in any one of the first to eighth aspects, the display control unit causes the result of the recognition to be displayed in a region suitable for the area, in a display region of the display apparatus. In the ninth aspect, the display control unit may cause the result of the recognition to be superimposed on the medical image, or may cause the result of the recognition to be displayed in a region outside the display region of the medical image in the display region. As a result of displaying the result of the recognition in a region suitable for the area, the recognition result can be appropriately displayed.

In a medical image processing apparatus according to a tenth aspect, in any one of the first to ninth aspects, the display control unit causes the display apparatus to display the medical image in a display mode suitable for the area. According to the tenth aspect, as a result of displaying the medical image in addition to the recognition result in a display mode suitable for the area, it is possible to perform more appropriate display.

In a medical image processing apparatus according to an eleventh aspect, in the tenth aspect, the display control unit causes the display apparatus to display the medical image at a display position and/or in a size suitable for the area information. The eleventh aspect defines one aspect of displaying a medical image in a manner suitable for the area.

In a medical image processing apparatus according to a twelfth aspect, in any one of the first to eleventh aspects, the medical image acquiring unit acquires, as the medical image, a medical image captured by using observation light in a wavelength range suitable for the area indicated by the area information, and the display control unit causes the display apparatus to display the result of the recognition for the medical image captured by using the observation light in the wavelength range. According to the twelfth aspect, use of the medical image captured by using the observation light in the wavelength range suitable for the area makes it possible to perform accurate recognition. For example, it is possible to use a medical image captured by using, as observation light, normal light (white light), special light (narrow-band light), or a combination of normal light and special light.

In a medical image processing apparatus according to a thirteenth aspect, in any one of the first to twelfth aspects, the medical image processing apparatus further includes a medical image processing unit that performs, on the medical image, image processing suitable for the area. The image processing suitable for the area makes it possible to generate a medical image with which accurate observation can be performed.

In a medical image processing apparatus according to a fourteenth aspect, in any one of the first to thirteenth aspects, the recognizer is a detector that detects a region of interest in the medical image. The detector can be constituted by, for example, a hierarchical network.

In a medical image processing apparatus according to a fifteenth aspect, in any one of the first to thirteenth aspects, the recognizer is a classifier that performs classification on the medical image. The classifier can be constituted by, for example, a hierarchical network.

In a medical image processing apparatus according to a sixteenth aspect, in any one of the first to thirteenth aspects, the recognizer is a measurer that performs measurement on the medical image. The measurer can be constituted by, for example, a hierarchical network.

In a medical image processing apparatus according to a seventeenth aspect, in any one of the first to sixteenth aspects, the display control unit causes the display apparatus to display the acquired area information. According to the seventeenth aspect, when input of area information is forgotten or when there is an error in automatic recognition of area information, the user can easily become aware of it. The display control unit is capable of causing area information to be displayed using characters, figures, symbols, and a combination thereof. The color or brightness of the area information may be changed.

In a medical image processing apparatus according to an eighteenth aspect, in any one of the first to seventeenth aspects, the medical image processing apparatus further includes an accepting unit that accepts a setting of a display mode from a user, and the display control unit causes the display apparatus to display the result of the recognition in the display mode set by the accepted setting. Accordingly, the user is capable of displaying the recognition result in a desired manner.

To achieve the above-described object, an endoscope system according to a nineteenth aspect of the present invention includes the medical image processing apparatus according to any one of the first to eighteenth aspects, the display apparatus, an endoscope that serves as the medical apparatus, that is to be inserted into the subject, and that has an imaging unit that sequentially captures the medical images, and a light source apparatus that irradiates the subject with observation light. The endoscope system according to the nineteenth aspect includes the medical image processing apparatus according to any one of the first to eighteenth aspects and is thus capable of displaying a recognition result of a medical image in a manner suitable for an area. In addition, a user is capable of easily grasping switching of the area as a recognition target. In the nineteenth aspect, it is possible to use, as observation light, normal light (white light), special light (narrow-band light), and a combination of normal light and special light. Preferably, the light source apparatus radiates observation light in a different wavelength range in accordance with the area.

To achieve the above-described object, a medical image processing method according to a twentieth aspect of the present invention is a medical image processing method for a medical image processing apparatus including a medical image acquiring unit that acquires a medical image from a medical apparatus that sequentially captures images of a plurality of areas in a living body of a subject, and a recognizer that performs recognition on the medical image. The medical image processing method includes a medical image acquisition step of acquiring the medical image, an area information acquisition step of acquiring area information indicating an area in the living body in the acquired medical image, a recognition step of performing recognition on the medical image, and a display control step of causing a display apparatus to display a result of the recognition in a mode suitable for the area indicated by the area information. According to the twentieth aspect, as in the first aspect, the recognition result of the medical image can be displayed in a manner suitable for the area. In addition, a user is capable of easily grasping switching of the area as a recognition target.

The medical image processing method according to the twentieth aspect may further include configurations similar to those according to the second to eighteenth aspects. In addition, a program that causes the medical image processing apparatus or a computer to execute the medical image processing method according to these aspects, and a non-transitory recording medium storing computer-readable code of the program are also included in an aspect of the present invention.

As described above, the medical image processing apparatus, the endoscope system, and the medical image processing method according to the present invention are capable of performing recognition and display of a recognition result in a manner suitable for an area.

BRIEF DESCRIPTION OF THE DRAWINGS

FIGS. 4A and 4B are diagrams illustrating configuration examples of a convolutional neural network;

DESCRIPTION OF THE PREFERRED EMBODIMENTS

Hereinafter, an embodiment of a medical image processing apparatus, an endoscope system, and a medical image processing method according to the present invention will be described in detail with reference to the accompanying drawings.

First Embodiment

Configuration of Endoscope System

Figure 1:
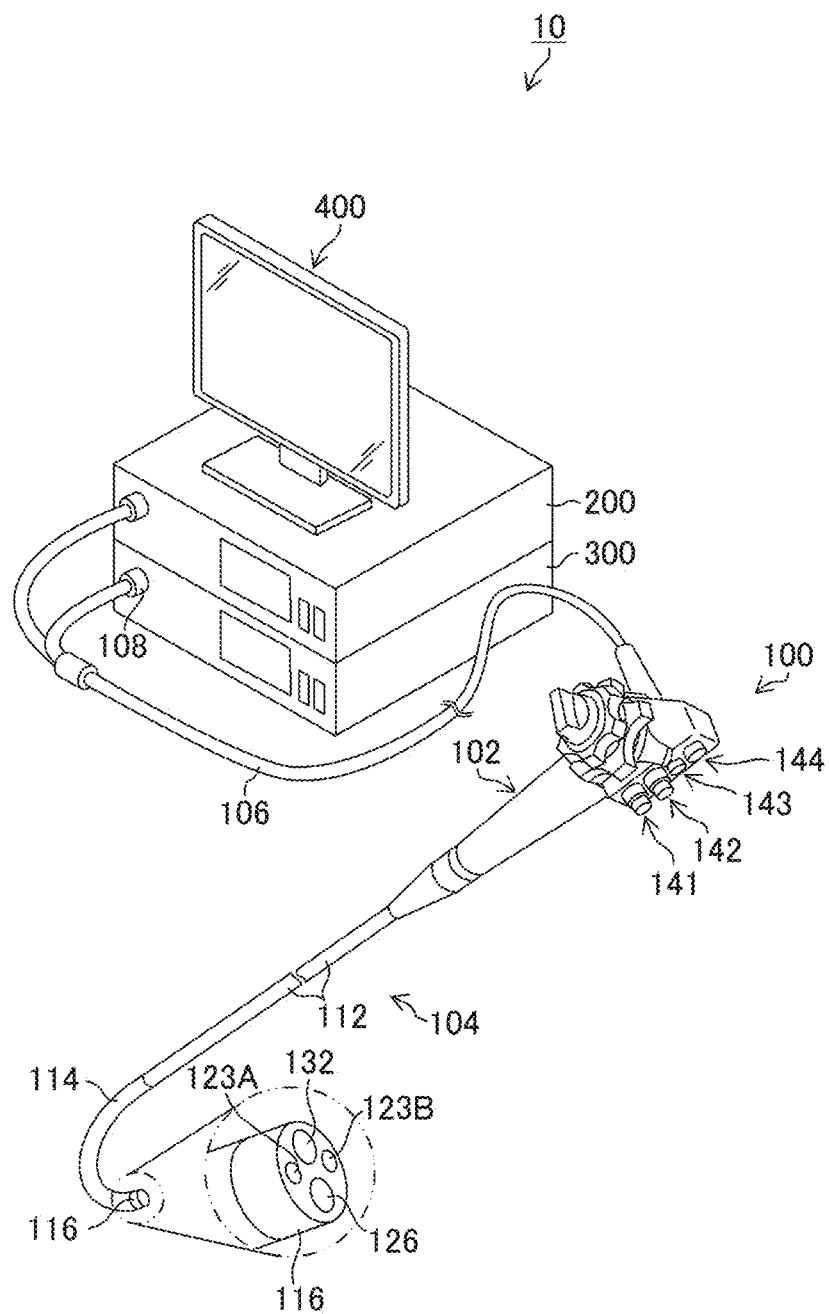
FIG. 1 is a diagram illustrating the configuration of an endoscope system according to a first embodiment.
Figure 2:
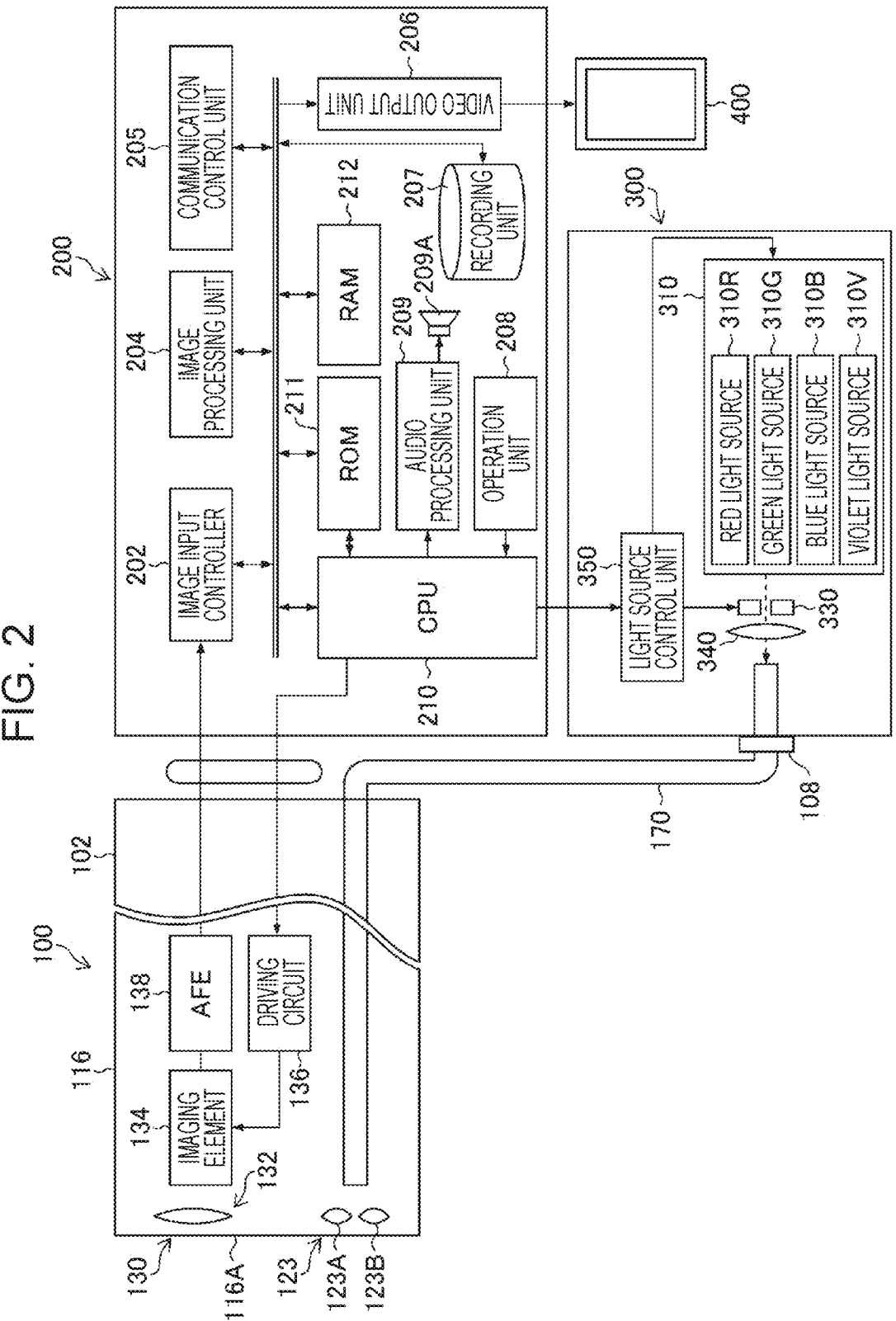
FIG. 2 is another diagram illustrating the configuration of the endoscope system.

FIG. 1 is an external appearance diagram of an endoscope system 10 (a medical image processing apparatus, an endoscope system), and FIG. 2 is a block diagram illustrating the configuration of a main part of the endoscope system 10. As illustrated in FIGS. 1 and 2, the endoscope system 10 is constituted by an endoscope 100 (a medical apparatus, an endoscope, an endoscope main body), an endoscope processor apparatus 200 (a medical image processing apparatus), a light source apparatus 300 (a light source apparatus), and a monitor 400 (a display apparatus). An external device (not illustrated) for acquiring area information by using an electromagnetic wave or an ultrasonic wave may be connected to the endoscope system 10.

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation or treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens, an imaging unit) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIGS. 1 and 2, the imaging lens 132 (an imaging unit) is disposed on a distal-end-side surface 116A of the tip rigid part 116. A complementary metal-oxide semiconductor (CMOS) imaging element 134 (an imaging element, an imaging unit), a driving circuit 136, and an analog front end (AFE) 138 (an imaging unit) are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. In the first embodiment, a description will be given of a case where the imaging element 134 is a CMOS imaging element, but the imaging element 134 may be a charge coupled device (CCD) imaging element. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the endoscope processor apparatus 200 through a signal cable that is not illustrated, and converted into a video signal. Accordingly, an endoscopic image is displayed on the monitor 400, which is connected to the endoscope processor apparatus 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

A user performs imaging (under control of the imaging unit and a medical image acquiring unit 220) at a determined frame rate while inserting or removing the endoscope 100 (the insertion section 104) having the above-described configuration into or from a living body as a subject, thereby being capable of sequentially capturing images of a plurality of areas in the living body.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and the violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type of photographic subject, an area of the photographic subject, the purpose of observation, or the like. It is also preferable that, during observation, the wavelengths of observation light be combined and/or switched in accordance with the type of photographic subject, an area of the photographic subject, the purpose of observation, or the like. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Endoscope Processor Apparatus

The configuration of the endoscope processor apparatus 200 will be described with reference to FIG. 2. In the endoscope processor apparatus 200, an image input controller 202 receives an image signal output from the endoscope 100, an image processing unit 204 (a medical image processing unit 234 or the like) performs necessary image processing thereon, and a video output unit 206 outputs a resulting image signal. Accordingly, an observation image (an inside-of-living-body image) is displayed on the monitor 400 (a display apparatus). These processing operations are performed under control by a central processing unit (CPU) 210. A communication control unit 205 controls communication, for a medical image or area information, with a hospital information system (HIS), a hospital local area network (LAN), and/or an external system or network that are not illustrated. In a recording unit 207 (a recording apparatus), an image of a subject (an endoscopic image, a medical image), area information, information indicating a result of recognition (detection, classification, measurement, etc.), and the like are recorded (see FIG. 6 and the description related thereto). An audio processing unit 209 outputs a message (sound) about recognition processing and a recognition result from a speaker 209A under control by the CPU 210 and the image processing unit 204.

A read only memory (ROM) 211 is a nonvolatile storage element (a non-transitory recording medium) and stores a computer-readable code of a program that causes the CPU 210 and/or the image processing unit 204 (a medical image processing apparatus, a computer) to execute various image processing methods. A random access memory (RAM) 212 is a storage element for temporary storage in various processing operations and can be used as a buffer at the time of acquiring an image.

A user is capable of providing an instruction to execute medical image processing or designating a condition necessary for the execution via the operation unit 208. A display control unit 230 is capable of causing the monitor 400 to display a screen of these instructions, a result of recognition, and so forth.

Functions of Image Processing Unit

Figure 3:
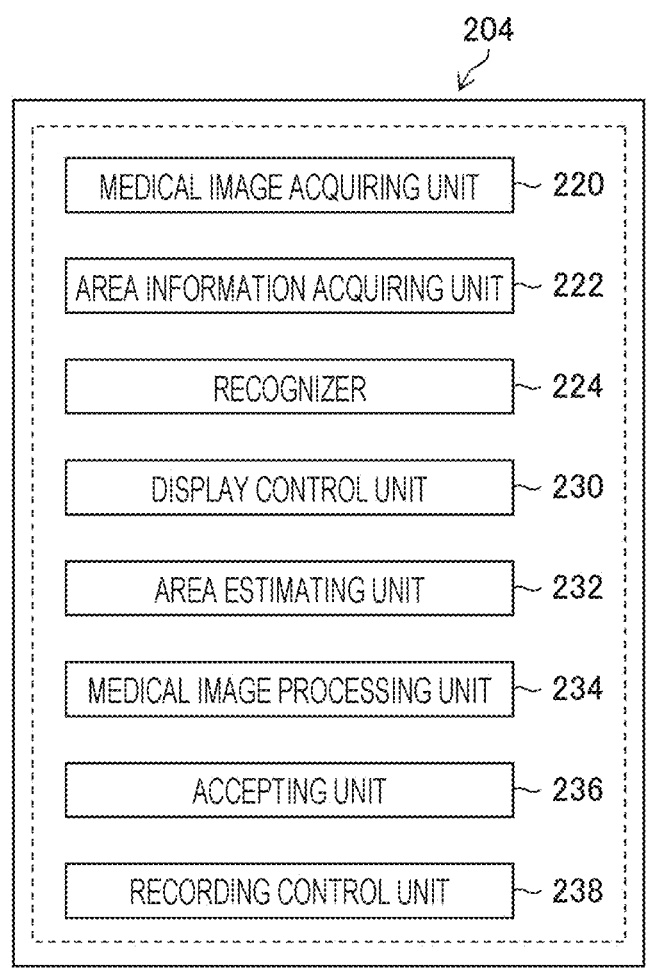
FIG. 3 is a functional block diagram of an image processing unit.

FIG. 3 is a functional block diagram of the image processing unit 204. The image processing unit 204 includes the medical image acquiring unit 220 (a medical image acquiring unit), an area information acquiring unit 222 (an area information acquiring unit), a recognizer 224 (a recognizer), the display control unit 230 (a display control unit), an area estimating unit 232 (an area estimating unit), the medical image processing unit 234 (a medical image processing unit), an accepting unit 236 (an accepting unit), and a recording control unit 238 (a recording control unit). Medical image processing performed using these functions will be described below in detail.

The image processing unit 204 is capable of performing, with the above-described functions, calculation of a feature quantity of a medical image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image. The above-described processing is performed under control by the CPU 210.

Implementation of Functions by Various Processors

The above-described functions of the individual units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as the read only memory (ROM) 211, and the computer refers to the software. The software stored in the non-transitory recording medium includes a program for executing the medical image processing method according to the present invention and data to be used for the execution (data about acquisition of area information, data used to specify a display mode, a parameter used in the recognizer, and so forth). The code may be recorded on a non-transitory recording medium, such as a magneto-optical recording device of various types or a semiconductor memory, instead of the ROM 211. In the processing using the software, the random access memory (RAM) 212 may be used as a transitory storage region, for example, and data stored in an electrically erasable and programmable read only memory (EEPROM) that is not illustrated can be referred to, for example. The recording unit 207 may be used as a "non-transitory recording medium".

Recognizer Using Learned Model

The above-described recognizer (a detector, a classifier, a measurer) can be constituted by using a learned model (a model learned by using an image set constituted by captured images of a living body), such as a convolutional neural network (CNN) or a support vector machine (SVM). Hereinafter, a description will be given of a layer configuration in a case where the recognizer is constituted by a CNN. The description will be given mainly of a detector (a recognizer that performs detection of a region of interest). However, a similar layer configuration can be adopted for classification (discrimination) or measurement.

Examples of Layer Configuration of CNN

FIGS. 4A and 4B are diagrams illustrating examples of the layer configuration of a CNN. In the example illustrated in FIG. 4A, a CNN 562 includes an input layer 562A, an intermediate layer 562B, and an output layer 562C. The input layer 562A receives an endoscopic image (medical image) acquired by the medical image acquiring unit 220 and outputs a feature quantity. The intermediate layer 562B includes convolutional layers 564 and pooling layers 565, and receives the feature quantity output from the input layer 562A and calculates another feature quantity. These layers each have a structure in which a plurality of "nodes" are connected by "edges" and hold a plurality of weight parameters. The values of the weight parameters change as learning progresses. The CNN 562 may include a fully connected layer 566 as in the example illustrated in FIG. 4B. The layer configuration of the CNN 562 is not limited to the configuration in which the convolutional layers 564 and the pooling layers 565 are alternately arranged, and may include a plurality of consecutive convolutional layers 564 or pooling layers 565 (for example, convolutional layers 564). Alternatively, a plurality of consecutive fully connected layers 566 may be included.

Processing in Intermediate Layer

The intermediate layer 562B calculates a feature quantity through convolutional operation and pooling processing. The convolutional operation performed in the convolutional layer 564 is processing of acquiring a feature map through convolutional operation using a filter, and plays a role in feature extraction such as edge extraction from an image. As a result of the convolutional operation using a filter, one-channel (one) "feature map" is created for one filter. The size of the "feature map" is scaled down by convolution and is reduced as convolution is performed in each layer. The pooling processing performed in the pooling layer 565 is processing of reducing (or enlarging) the feature map output through the convolutional operation to create a new feature map, and plays a role in giving robustness so that the extracted feature is not affected by parallel movement or the like. The intermediate layer 562B can be constituted by one or a plurality of layers that perform these processing operations.

Figure 5:
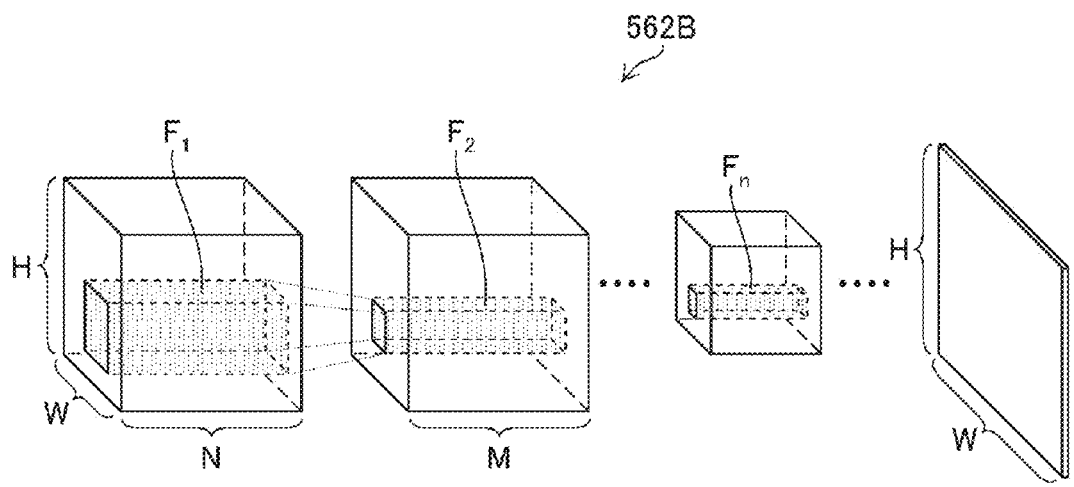
FIG. 5 is a diagram illustrating a state of convolutional processing using filters.

FIG. 5 is a schematic diagram illustrating an example configuration of the intermediate layer 562B of the CNN 562 illustrated in FIGS. 4A and 4B. In the first convolutional layer of the intermediate layer 562B, convolutional operation of an image set constituted by a plurality of medical images (a learning image set in the case of learning, and a recognition image set in the case of recognition) and a filter $F_1$ is performed. The image set is constituted by N (N-channel) images each having an image size in which the height is represented by H and the width is represented by W. In the case of inputting normal-light images, the images constituting a data set are three-channel images of red (R), green (G), and blue (B). The filter $F_1$ convoluted with this image set has a filter size of 5×5×N in the case of the filter having size 5 (5×5), for example, because the image set has N channels (N images). As a result of convolutional operation using the filter $F_1$, one-channel (one) "feature map" is created for one filter $F_1$. A filter $F_2$ used in the second convolutional layer has a filter size of 3×3×M in the case of the filter having size 3 (3×3), for example.

As in the first convolutional layer, in the second to n-th convolutional layers, convolutional operations using filters $F_2$ to $F_n$ are performed, respectively. The size of the "feature map" in the n-th convolutional layer is smaller than the size of the "feature map" in the second convolutional layer because scaling-down is performed in the convolutional layers or pooling layers in the preceding stages.

In the layers of the intermediate layer 562B, lower-order feature extraction (extraction of edges or the like) is performed in a convolutional layer near the input side, and higher-order feature extraction (extraction of features about the shape, structure, and the like of an object) is performed near the output side. In the case of performing segmentation for the purpose of measurement or the like, scaling-up is performed in a convolutional layer in a latter-half portion, and the "feature map" having the same size as the input image set can be obtained in the last convolutional layer. On the other hand, in the case of performing object detection, it is sufficient to output position information and thus scaling-up is not necessary.

The intermediate layer 562B may include a layer for performing batch normalization in addition to the convolutional layers 564 and the pooling layers 565. Batch normalization processing is the processing of normalizing a data distribution in units of mini batches for performing learning, and plays a role in quickly performing learning, reducing dependency on an initial value, suppressing overtraining, and so forth.

Processing in Output Layer

The output layer 562C is a layer that detects the position of a region of interest depicted in an input medical image (a normal-light image, a special-light image) on the basis of the feature quantity output from the intermediate layer 562B and outputs the result thereof. In the case of performing segmentation, the output layer 562C grasps the position of a region of interest depicted in an image in the pixel level by using the "feature map" acquired from the intermediate layer 562B. That is, the output layer 562C is capable of detecting, for each pixel of an endoscopic image, whether or not the pixel belongs to the region of interest, and outputting the detection result. On the other hand, in the case of performing object detection, determination in the pixel level is not necessary, and the output layer 562C outputs position information of a target.

The output layer 562C may execute discrimination (classification) of a lesion and output a discrimination result. For example, the output layer 562C may classify an endoscopic image into three categories "neoplastic", "non-neoplastic", and "others", and may output, as a discrimination result, three scores corresponding to "neoplastic", "non-neoplastic", and "others" (the sum of the three scores is 100%), or may output a classification result in a case where the endoscopic image can be clearly classified from the three scores. In the case of outputting a discrimination result, the output layer 562C may or may not include a fully connected layer as the last one or plural layers (see FIG. 4B).

The output layer 562C may output a measurement result of a region of interest. In the case of performing measurement by using the CNN, for example, the region of interest as a target may be segmented in the above-described manner and then measurement can be performed by the image processing unit 204 or the like on the basis of the result thereof. Alternatively, a measurement value of the region of interest as a target can be output directly from the recognizer 224. In the case where the measurement value is directly output, the image is caused to learn the measurement value, and thus regression of the measurement value occurs.

In the case of using the CNN having the above-described configuration, it is preferable to perform, in a learning procedure, a process of comparing a result output from the output layer 562C with a correct answer of recognition for the image set to calculate loss (error), and updating the weight parameters in the intermediate layer 562B from the layer on the output side toward the layer on the input side so that the loss is reduced (backpropagation).

Recognition Using Method Other than CNN

The recognizer 224 may perform recognition (detection or the like of a region of interest) by using a method other than the CNN. For example, a region of interest can be detected on the basis of a feature quantity of pixels of an acquired medical image. In this case, the recognizer 224 divides a detection target image into, for example, a plurality of rectangular regions, sets the rectangular regions obtained through the division as local regions, calculates, for each local region in the detection target image, a feature quantity (for example, hue) of pixels in the local region, and determines a local region having a specific hue among the local regions as a region of interest. Similarly, the recognizer 224 may perform classification or measurement based on a feature quantity.

Information Recorded in Recording Unit

Figure 6:
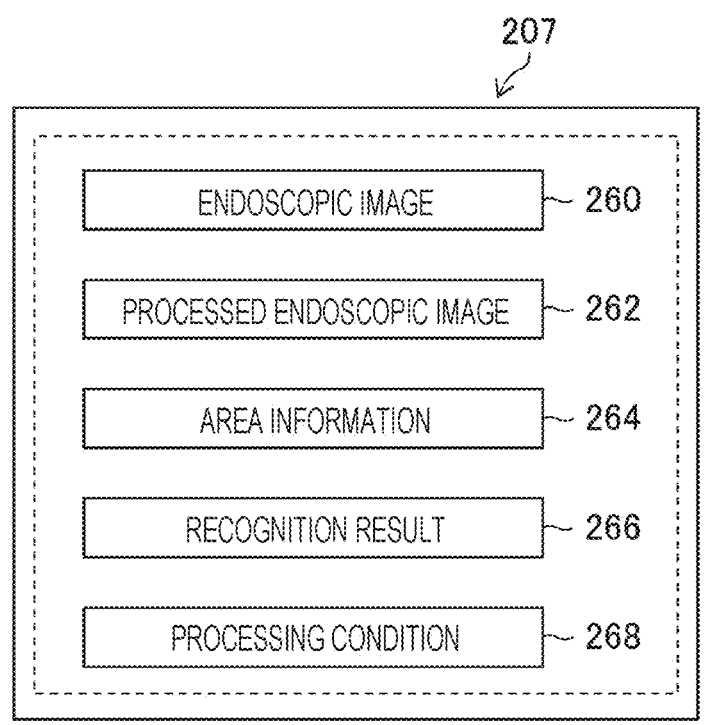
FIG. 6 is a diagram illustrating information recorded in a recording unit.

FIG. 6 is a diagram illustrating an example of information recorded in the recording unit 207. In the example in FIG. 6, an endoscopic image 260 (a medical image), a processed endoscopic image 262 (a medical image) on which image processing has been performed, area information 264 (area information indicating an area in a living body whose medical image has been captured), a recognition result 266 (a result of recognition: detection, classification, measurement, etc.), and a processing condition 268 (a condition for performing recognition or display of a result) are recorded. Other information may also be recorded. The recording control unit 238 records these pieces of information in association with each other.

Medical Image Processing Method

Figure 7:
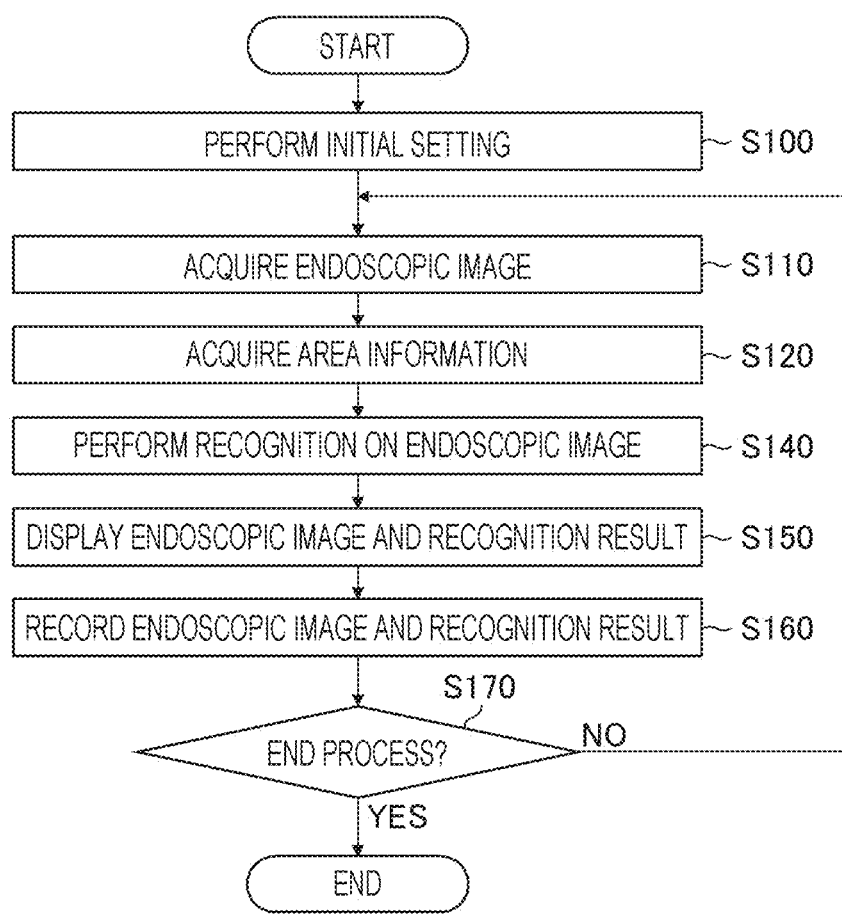
FIG. 7 is a flowchart illustrating a procedure of a medical image processing method according to the first embodiment.

A medical image processing method for the endoscope system 10 having the above-described configuration will be described. FIG. 7 is a flowchart illustrating a procedure of the medical image processing method according to the first embodiment. Hereinafter, a description will be given of a case where the recognizer 224 serves as a detector. The processing can be performed in a similar manner in a case where the recognizer 224 serves as a classifier or a measurer.

Initial Setting

The accepting unit 236 (an accepting unit) sets conditions necessary for execution on the basis of a user operation performed using the operation unit 208 and/or the processing condition 268 (for example, a default processing condition) recorded in the recording unit 207 (step S100: an initial setting step). For example, the accepting unit 236 sets an area information acquisition method, such as a display mode (characters, figures, or symbols to be displayed, and the color thereof), whether a recognition result is to be displayed or not to be displayed, a condition for display or non-display (an area for which a recognition result is to be displayed, an area for which a recognition result is not to be displayed, etc.), and the relationship between area information and a display mode (for example, a display position and/or a size). The conditions may be set or changed during execution of the following steps.

Acquisition of Endoscopic Image

The medical image acquiring unit 220 (a medical image acquiring unit) acquires an endoscopic image (a medical image) captured in the living body of a subject (step S110: a medical image acquisition step). The medical image acquiring unit 220 is capable of acquiring an endoscopic image in real time by sequentially capturing images of the inside of the living body as the subject at a predetermined frame rate by using the imaging unit (the imaging lens 132, the imaging element 134, the AFE 138, and so forth) of the endoscope 100 (a medical apparatus). The medical image acquiring unit 220 may acquire, in non-real time, an endoscopic image that has already been captured and recorded. For example, the medical image acquiring unit 220 may acquire the endoscopic image 260 or the processed endoscopic image 262 recorded in the recording unit 207, or may acquire an image from an external apparatus or system via the communication control unit 205. In a case where area information has already been acquired (for example, in a case where the process to step S170 is executed once or more and then the process is continued from step S110), the medical image acquiring unit 220 may acquire an endoscopic image (a medical image) captured by using observation light in a wavelength range suitable for the area indicated by the area information. For example, an image captured by using white light can be acquired in the case of the stomach, and an image captured by using blue narrow-band light can be acquired in the case of the esophagus. The display control unit 230 causes the monitor 400 to display the acquired endoscopic image.

Acquisition of Area information

The area information acquiring unit 222 (an area information acquiring unit) acquires area information indicating an area in the living body whose endoscopic image has been captured (step S120: an area information acquisition step). The area information acquiring unit 222 is capable of acquiring the area information by analyzing the endoscopic image, by using area information input by the user, or by using information from an external device different from the medical image acquiring unit 220. Which method is to be used to acquire the area information can be determined on the basis of the conditions set in step S100. In the case of analyzing the endoscopic image, the area information acquiring unit 222 (an area information acquiring unit) is capable of performing analysis by using a feature quantity, such as a color, of the photographic subject. A learned model (CNN, SVM, or the like) for analysis may be used. In the case of using a user input, information input via the operation unit 208 can be used. As the "external device", a device that observes an insertion area of the endoscope by using an electromagnetic wave, an ultrasonic wave, radiation, or the like can be used. In this case, the area estimating unit 232 (an area estimating unit) is capable of estimating an area by using information acquired by the external device (see the example illustrated in FIGS. 19A and 19B).

Recognition on Image

The recognizer 224 performs recognition on the endoscopic image (a medical image) (step S140: a recognition step). In the case of detecting a region of interest, as described above, the recognizer 224 is capable of grasping the position of the region of interest in the image in the pixel level (that is, detecting, for each pixel of the endoscopic image, whether the pixel belongs to the region of interest) by using the "feature map", and outputting a detection result. Examples of the region of interest (region of concern) to be detected may include a polyp, a cancer, a colon diverticulum, an inflammation, a treatment scar (a scar of endoscopic mucosal resection (EMR), a scar of endoscopic submucosal dissection (ESD), a clip portion, or the like), a bleeding point, a perforation, angiodysplasia, and the like.

Display of Endoscopic Image and Recognition Result

The display control unit 230 (a display control unit) causes the monitor 400 (a display apparatus) to display the endoscopic image and the result of recognition in a mode suitable for the area indicated by the area information (step S150: a display control step). As will be illustrated in the following modes, the display control unit 230 may change the shape, color, size, position, or the like of a figure to be superimposed on the endoscopic image in accordance with the area, may change the display mode of the area information, or may apply a combination thereof.

First Display Mode

For example, the tint of a mucous membrane is significantly different between the esophagus and the stomach, and thus a detection result can be made more conspicuous by superimposing a figure having a color suitable for each area. In addition, as compared to the esophagus covered with a squamous epithelium, the stomach may have a complex and minute state change, such as inflammation or contraction, and thus it is necessary to observe the stomach in more detail. Thus, in the case of the stomach, it is not preferable to use a method of superimposing a figure or the like directly on an endoscopic image.

Figure 8A:
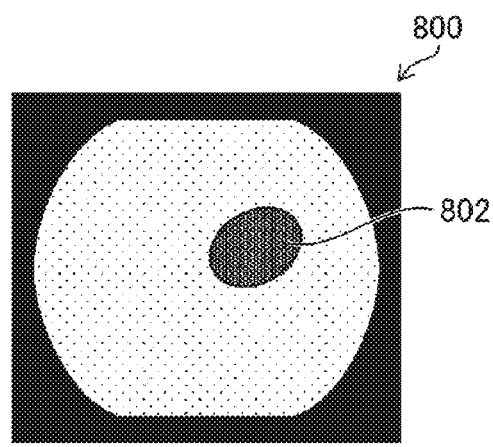
FIGS. 8A to 8D are diagrams illustrating examples of emphasized display suitable for an area.
Figure 8B:
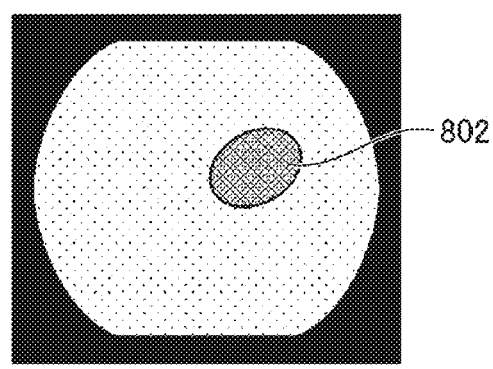
Figure 8C:
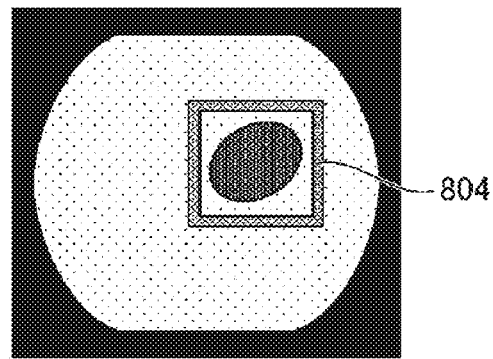
Figure 8D:
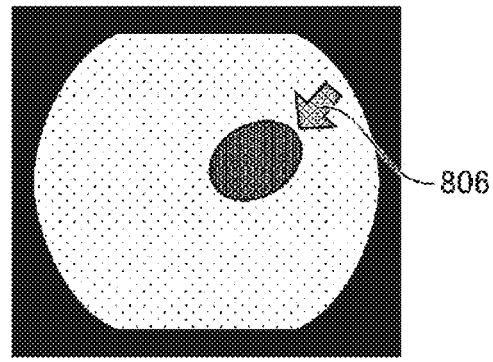
Figure 9A:
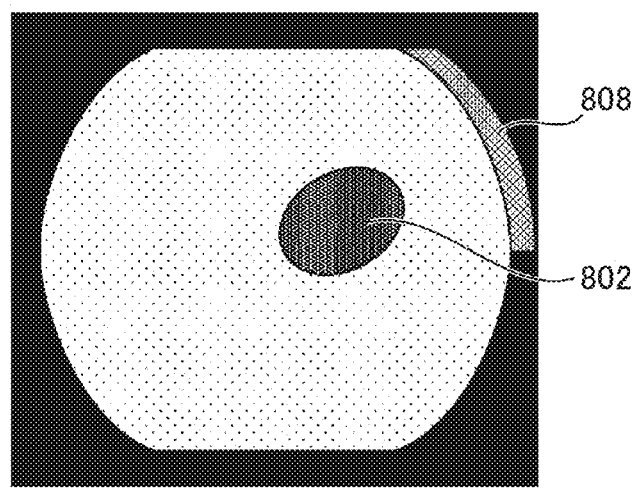
FIGS. 9A to 9C are other diagrams illustrating examples of emphasized display suitable for an area.
Figure 9B:
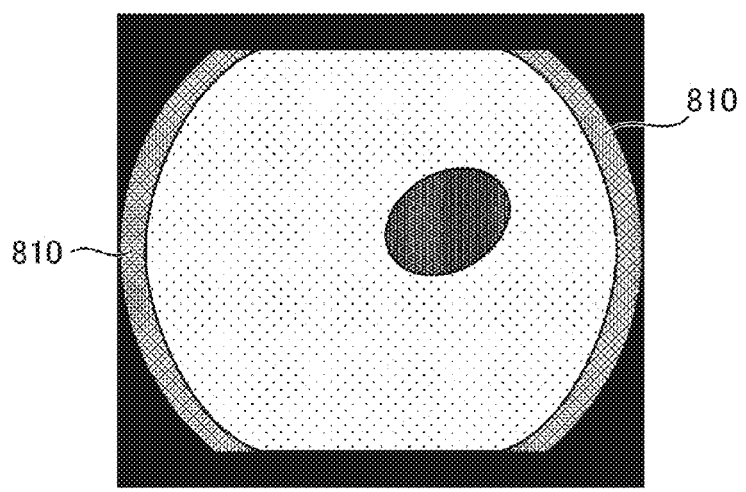
Figure 9C:
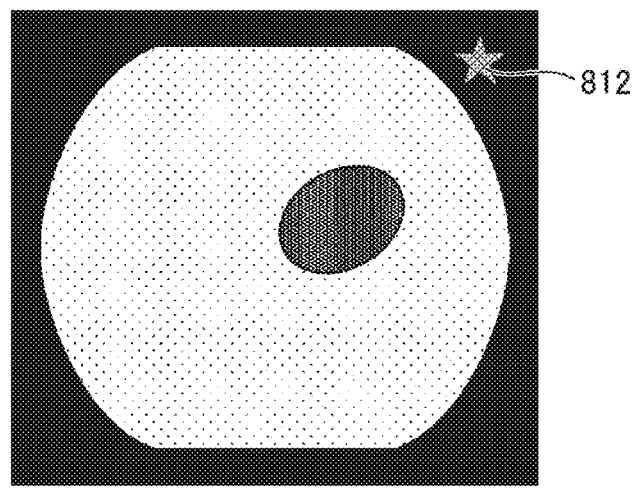

FIGS. 8A to 9C are diagrams illustrating display modes implemented in consideration of these circumstances. FIGS. 8A to 8D illustrate states in which a figure is superimposed directly on an endoscopic image 800. FIG. 8B illustrates an example in which a region of interest 802 is solid filled, FIG. 8C illustrates an example in which the region of interest 802 is enclosed in a FIG. 804, and FIG. 8D illustrates an example in which an arrow 806 is displayed. Such conspicuous display modes can be used in the case of the esophagus, for example. FIG. 8A is a diagram illustrating a state in which emphasized display is not performed (for reference), and the region of interest 802 is depicted in the endoscopic image 800. In contrast, in the examples illustrated in FIGS. 9A to 9C, in a display region of the monitor 400 (a display apparatus), a recognition result is displayed in a region suitable for the area (a figure or the like is not directly superimposed on the endoscopic image, but is displayed outside a display range of the endoscopic image in the display region of the monitor 400). FIG. 9A illustrates an example in which a frame 808 is displayed at the upper right of the display region, FIG. 9B illustrates an example in which a frame 810 is displayed on the right and left of the display region, and FIG. 9C illustrates an example in which a star-shaped symbol 812 is displayed at the upper right of the display region. With use of such modes in the case of the stomach, for example, the user is capable of observing the mucous membrane in more detail while the observation is not hindered by the display of the recognition result. The recognition result may be displayed or hidden by the above-described condition setting according to an area. In a case where a setting is made to hide the recognition result, the mode in which "recognition is performed but the result is not displayed" is possible. Alternatively, the recognition result may be displayed or hidden in accordance with a determined condition (an elapsed time or the like) other than an area. Furthermore, the display mode may be changed (the figure may be changed, the color or brightness may be changed, or the like) in accordance with a recognition result and/or the certainty thereof.

Figure 10:
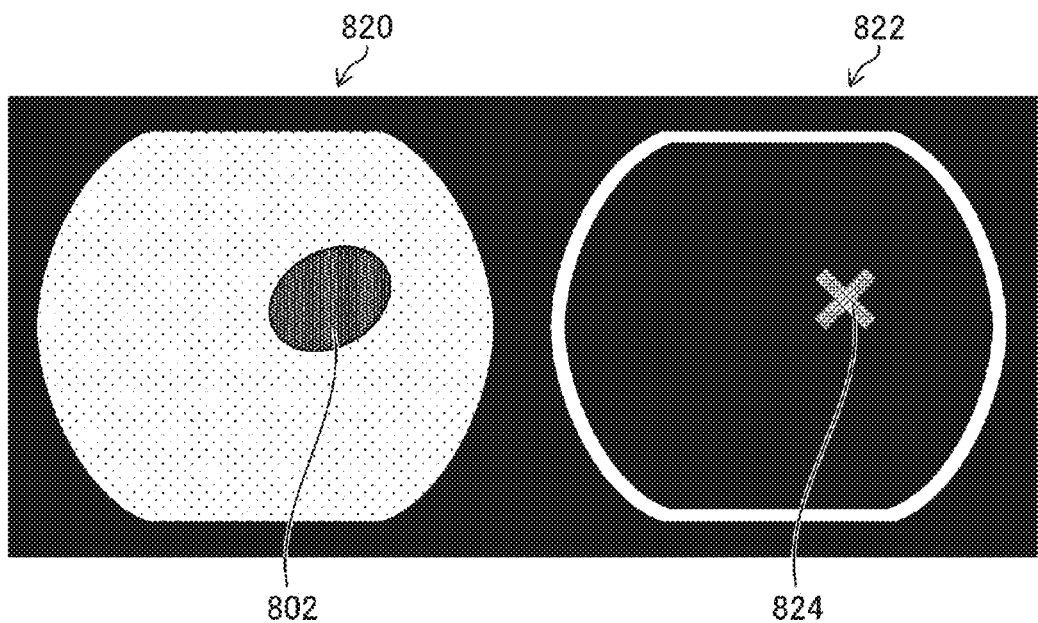
FIG. 10 is still another diagram illustrating an example of emphasized display suitable for an area.

The endoscopic image and the recognition result may be displayed on a single screen as in the examples in FIGS. 8A to 9C, or may be displayed on two screens as in the example in FIG. 10. In the example in FIG. 10, an endoscopic image 820 and a recognition result display image 822 are displayed by using two screens. In the recognition result display image 822, a symbol 824 is displayed at the position corresponding to the region of interest 802. In the case of using two or more screens for display, different screens on the same monitor may be used for split display, or a plurality of monitors may be used for display. In the case of changing the display mode from the mode using two screens as illustrated in FIG. 10 to the mode using a single screen as illustrated in FIGS. 8A to 9C, the display position and/or the size of an observation screen (the endoscopic image, the recognition result) may also be changed. This makes it possible to display the observation screen while fully utilizing the monitor size.

The medical image acquiring unit 220 may acquire, as a medical image, an endoscopic image (a medical image) captured by using observation light in a wavelength range suitable for the area indicated by area information, and the display control unit 230 may cause the monitor 400 (a display apparatus) to display a result of recognition for the medical image captured by using the observation light in the wavelength range. For example, an image captured by using white light (normal light) can be provided for recognition in the case of the stomach, and an image captured by using special light (blue narrow-band light), such as BLI (Blue Laser Imaging: registered trademark), can be provided for recognition in the case of the esophagus. In accordance with an area, an image captured by using special light, such as LCI (Linked Color Imaging: registered trademark), and subjected to image processing (in the case of LCI, a difference in chroma or hue of a color close to the color of the mucous membrane is extended) may be used. The image processing suitable for the area can be performed by the medical image processing unit 234 (a medical image processing unit).

As described above, the endoscope system 10 performs recognition and display of a recognition result suitable for an area, and is thus capable of presenting an image optimum to a user.

Second Display Mode

Figure 11A:
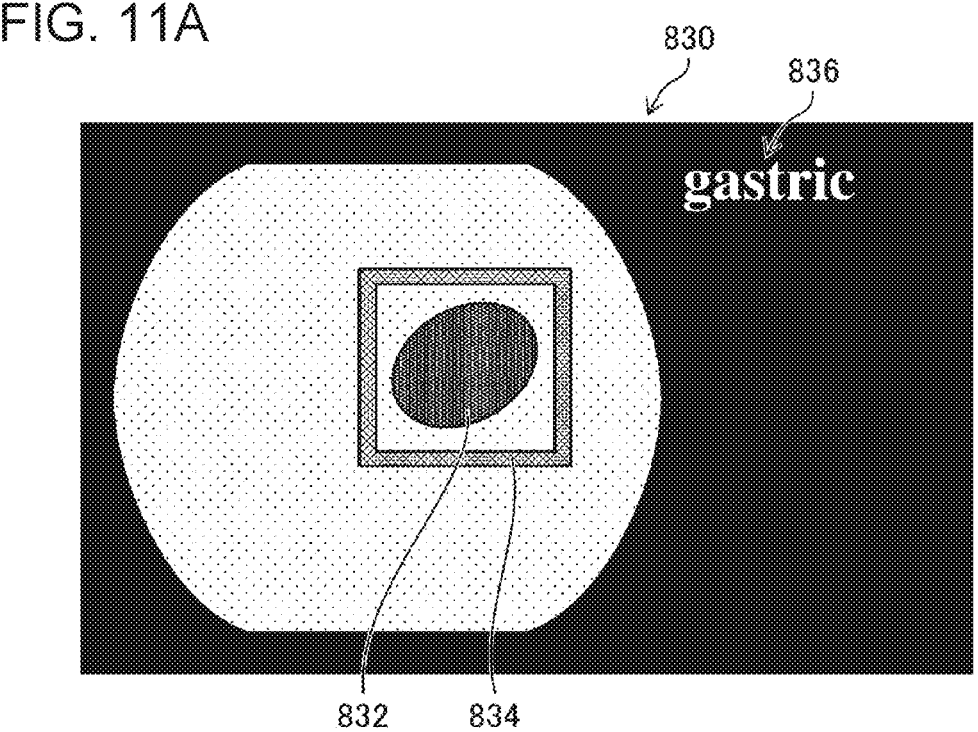
FIGS. 11A and 11B are diagrams illustrating display examples of area information.
Figure 11B:
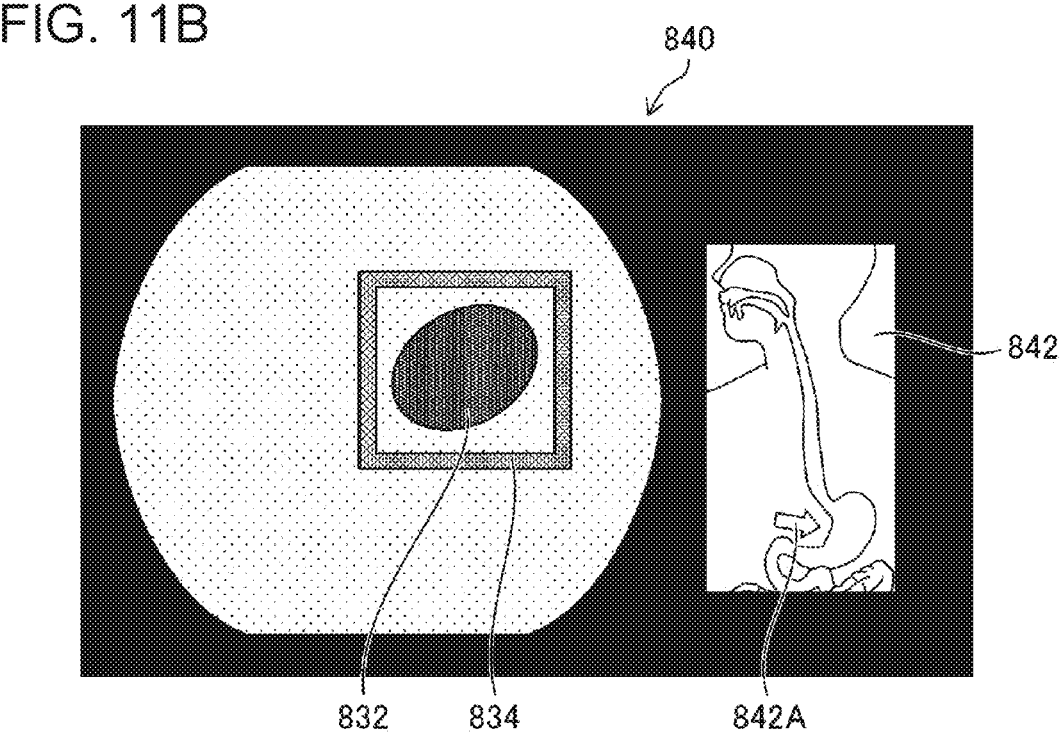

In a second display mode, the display control unit 230 (a display control unit) causes the monitor 400 to display area information acquired by the area information acquiring unit 222 (step S150: an area information display step, a display control step). FIGS. 11A and 11B are diagrams illustrating display examples of area information. FIG. 11A illustrates an example in which area information 836 is displayed as a text ("gastric") in addition to a frame 834 enclosing a region of interest 832 in an endoscopic image 830. FIG. 11B illustrates an example in which area information is represented by an arrow 842A on a schematic diagram 842 in an endoscopic image 840. Alternatively, the area information may be represented by an icon, and the display mode (the details, the position, the shape, the color, or the like of characters or symbols) may be changed according to an area. Display of such area information enables the user to become aware of a recognition error in a case where area information is automatically recognized from an observation image (acquired through image analysis), and enables the user to become aware that input has not been performed in a case where area information is acquired through input by the user. In the second display mode, the process of acquiring area information and performing recognition can be performed in a manner similar to that in the first display mode.

The display modes using a symbol, a figure, or the like illustrated in FIGS. 8A to 11B are merely examples. A display mode different from these examples may be adopted in accordance with a setting operation or the like performed by the user.

Recording of Recognition Result and so Forth

The recording control unit 238 (a recording control unit) records the endoscopic image and the recognition result as the endoscopic image 260 and the recognition result 266, respectively, in the recording unit 207 (step S160: a recording control step). In a case where image processing has been performed on the endoscopic image, the processed endoscopic image 262 can be recorded, and the area information 264 and/or the processing condition 268 may be recorded together with the endoscopic image 260 and the recognition result 266. It is preferable to record these pieces of information in association with each other. The image processing unit 204 determines whether or not to end the process (step S170). If the process is to be continued, the process returns to step S110, and the above-described process is performed on the next frame, for example.

The above-described acquisition of an endoscopic image and area information, recognition on the endoscopic image, and display of the endoscopic image and a recognition result can be performed for each frame of the endoscopic image. Thus, when an observation area changes in accordance with insertion or removal of the endoscope 100, the display mode of a recognition result changes in accordance with the change in the observation area. Accordingly, in the endoscope system 10 according to the first embodiment, a recognition result of a medical image can be displayed in a manner suitable for an area. In addition, a user is capable of easily grasping switching of the area as a recognition target.

Regarding display of a recognition result, a step of determining whether or not the area indicated by the area information acquired in step S120 is different from the preceding area (for example, in a case where image capturing is continuously performed at a determined frame rate, an area in a past frame (an immediately preceding frame or the like) having a difference in capturing timing smaller than or equal to a threshold value) (a determination step), and a step of resetting a display mode if the area has been changed (a resetting step) may be provided. The determination and resetting can be performed by the image processing unit 204 (for example, the area information acquiring unit 222 and the display control unit 230).

Second Embodiment

In the first embodiment, a description has been given of a case where the recognizer 224 is a single recognizer. In a second embodiment, a recognizer includes a plurality of recognizers each of which performs recognition on a medical image and corresponds to one of a plurality of areas in a living body. A recognizer selected from among the plurality of recognizers in accordance with the area indicated by area information performs recognition on a medical image.

Figure 12:
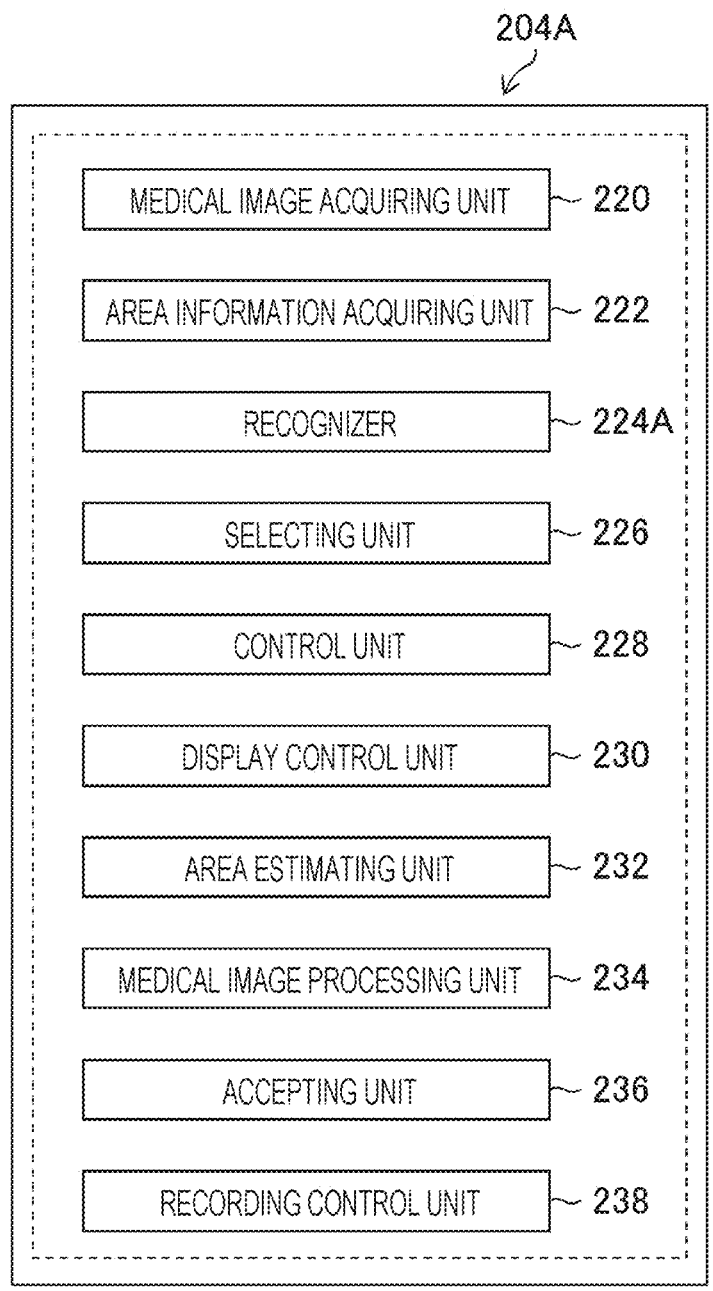
FIG. 12 is a functional block diagram of an image processing unit according to a second embodiment.

FIG. 12 is a diagram illustrating a functional configuration of an image processing unit 204A in an endoscope system according to the second embodiment. The image processing unit 204A is different from the image processing unit 204 according to the first embodiment (see a FIG. 3) in including a selecting unit 226 (a selecting unit) and a control unit 228 (a control unit) and in that a recognizer 224A includes a plurality of recognizers as will be described below. Other than that, the configuration of the endoscope system according to the second embodiment is similar to that of the endoscope system 10 according to the first embodiment, and thus the detailed description thereof is omitted.

Configuration of Recognizer

Figure 13:
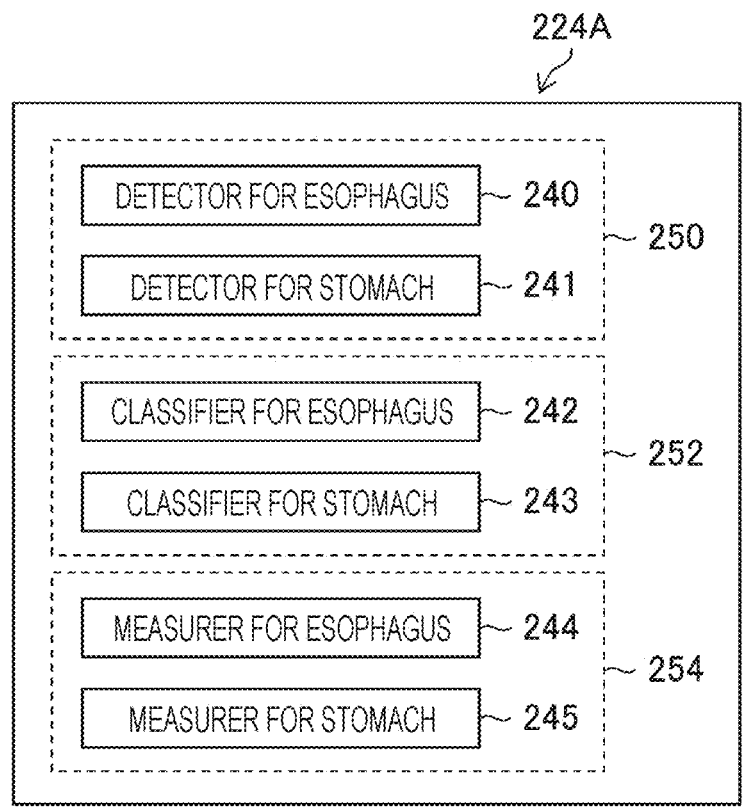
FIG. 13 is a diagram illustrating a configuration example of a recognizer according to the second embodiment.

In the endoscope system (an endoscope system, a medical image processing apparatus) according to the second embodiment, a "recognizer" includes a plurality of recognizers each of which performs recognition on a medical image and corresponds to one of a plurality of areas in a living body, and can be constituted by a detector, a classifier (a discriminator), a measurer, and a combination thereof. FIG. 13 is a diagram illustrating an example of a recognizer constituted by a plurality of recognizers that perform different types of recognition (a detector, a classifier, and a measurer). In the example in FIG. 13, the recognizer 224A includes a detector 250, a classifier 252, and a measurer 254 each of which has a plurality of recognizers corresponding to a plurality of organs (an aspect of areas). Specifically, the detector 250 has a detector for esophagus 240 and a detector for stomach 241, the classifier 252 has a classifier for esophagus 242 and a classifier for stomach 243, and the measurer 254 has a measurer for esophagus 244 and a measurer for stomach 245.

Figure 14:
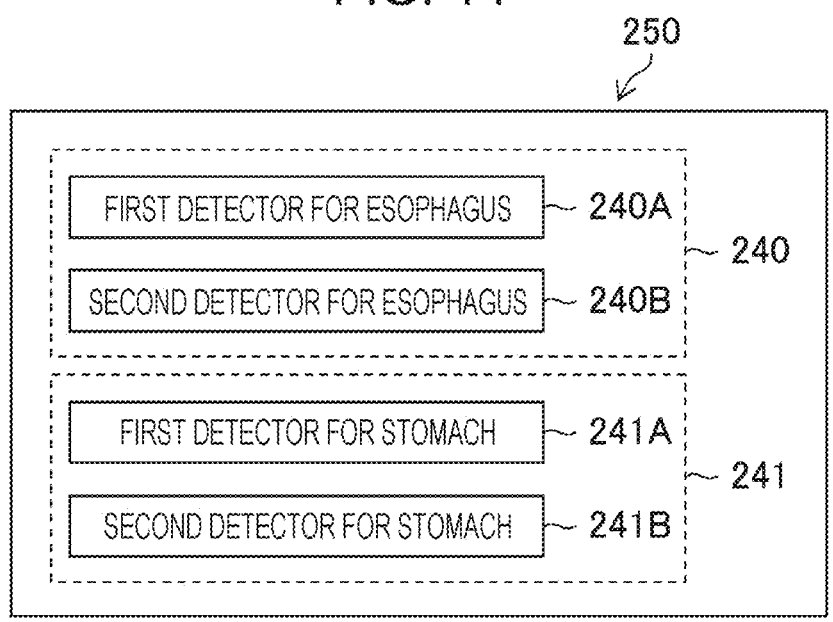
FIG. 14 is another diagram illustrating a configuration example of a recognizer according to the second embodiment.

FIG. 14 is a diagram illustrating the configuration of the detector 250. The detector 250 has a plurality of detectors (an aspect of recognizers) corresponding to different positions (an aspect of areas) of the same organ. Specifically, the detector for esophagus 240 has a first detector for esophagus 240A (for an upper portion of the esophagus) and a second detector for esophagus 240B (for a lower portion of the esophagus), and the detector for stomach 241 has a first detector for stomach 241A (for an upper portion of the stomach) and a second detector for stomach 241B (for a lower portion of the stomach). Similarly, the classifier 252 and the measurer 254 can be constituted by a plurality of classifiers and a plurality of measurers, respectively. FIG. 14 illustrates a case where two detectors (for an upper portion and a lower portion) are provided for each organ. Alternatively, three or more detectors may be provided for each organ (see a description of the case of performing recognition for the large intestine, which will be given below).

Note that "a plurality of areas" means organs (esophagus, stomach, small intestine, large intestine, and so forth) and/or a plurality of areas at different positions in an organ, and that a case where a distance (depth) from a surface is different at the same position of the same organ is not included in "difference in area".

Figure 15:
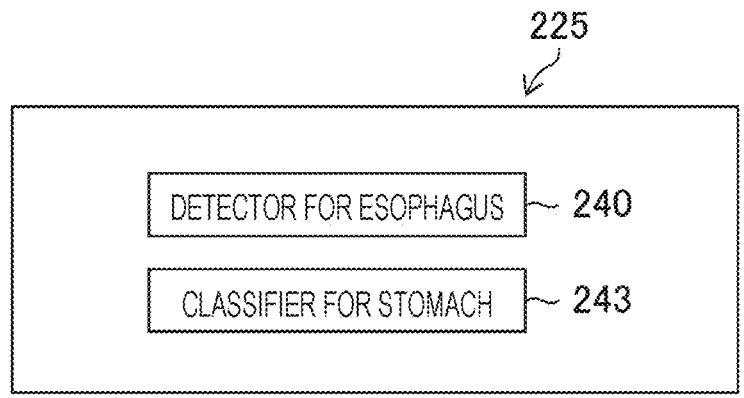
FIG. 15 is still another diagram illustrating a configuration example of a recognizer according to the second embodiment.

FIGS. 13 and 14 illustrate an aspect in which a plurality of recognizers that perform different types of recognition are provided for a plurality of areas. Alternatively, only a recognizer that performs a specific type of recognition (detection, classification, or measurement) may be provided for a specific organ. For example, an aspect in which "a detector is provided for the esophagus, and a classifier is provided for the stomach" is possible. Specifically, as illustrated in FIG. 15, a recognizer 225 may be constituted by the detector for esophagus 240 and the classifier for stomach 243 (the aspect described above with reference to FIGS. 13 and 14 can be adopted for the detector for esophagus 240 and the classifier for stomach 243). The recognizer 225 has a recognizer for esophagus and a recognizer for stomach, and is an aspect of "a plurality of recognizers each of which corresponds to one of a plurality of areas in a living body" in the medical image processing apparatus according to the present invention.

Learning with Image Set Corresponding to Area

Like the recognizer 224 according to the first embodiment, the recognizer 224A and the recognizer 225 can be constituted by using a plurality of learned models, such as CNN or SVM. Preferably, the plurality of learned models are different models that have learned by using image sets constituted by captured images of different areas in a living body in accordance with the areas as targets to be recognized. For example, the first detector for esophagus 240A and the second detector for esophagus 240B are models that have learned by using an image set constituted by captured images of an upper portion of the esophagus and an image set constituted by captured images of a lower portion of the esophagus, respectively. The first detector for stomach 241A and the second detector for stomach 241B are models that have learned by using an image set constituted by captured images of an upper portion of the stomach and an image set constituted by captured images of a lower portion of the stomach, respectively. Similarly, the classifier for esophagus 242 and the classifier for stomach 243, and the measurer for esophagus 244 and the measurer for stomach 245, are models for classification and measurement, respectively, each of which has learned by using an image set constituted by captured images of the esophagus or the stomach. Like the recognizer 224A, the recognizer 225 is a model that has learned by using image sets constituted by captured images of different areas according to the areas as targets to be recognized. As a result of performing learning by using an image set corresponding to an area, accurate recognition can be performed in accordance with the area.

Selection of Recognizer

Figure 16:
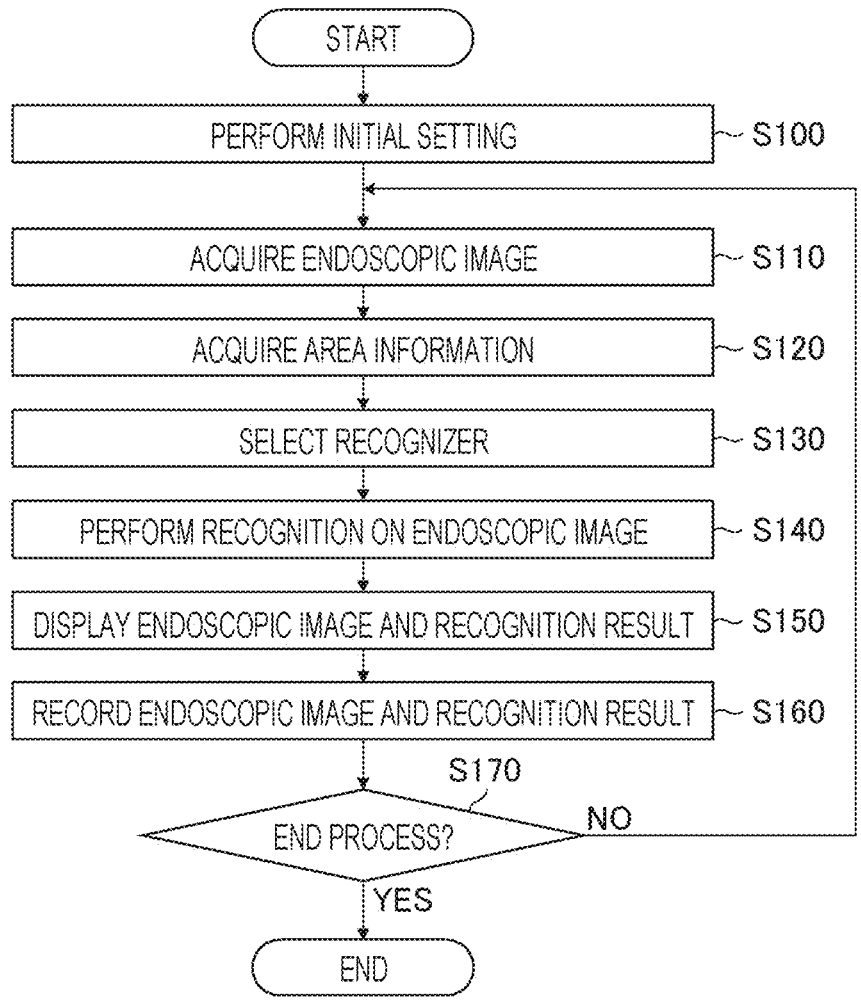
FIG. 16 is a flowchart illustrating a procedure of a medical image processing method according to the second embodiment.

FIG. 16 is a flowchart illustrating a procedure of a medical image processing method according to the second embodiment. This flowchart includes a step of selecting a recognizer (step S130: a selection step). The other steps are similar to those in the first embodiment, and thus the detailed description thereof is omitted. In step S130, the selecting unit 226 (a selecting unit) selects a recognizer corresponding to the area indicated by the area information from among the plurality of recognizers. In the endoscope system according to the second embodiment, a recognizer can be selected from among the recognizers constituting the recognizer 224A or the recognizer 225 (see FIGS. 13 to 15).

Control of Recognizer

Figure 17:
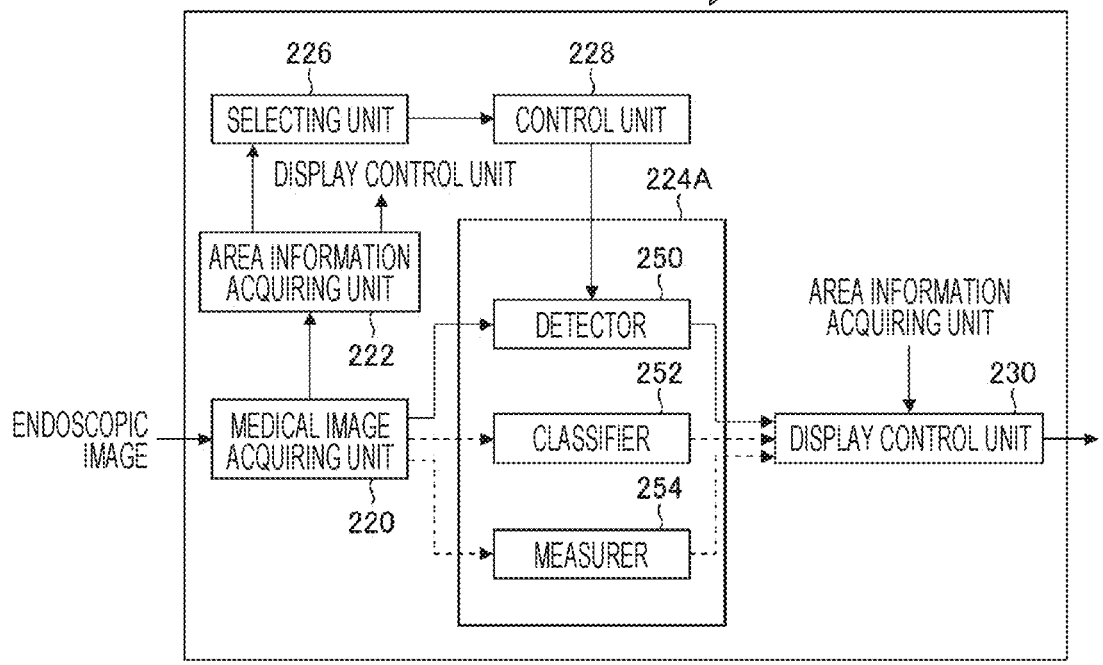
FIG. 17 is a diagram illustrating a state of controlling a recognizer.
Figure 18:
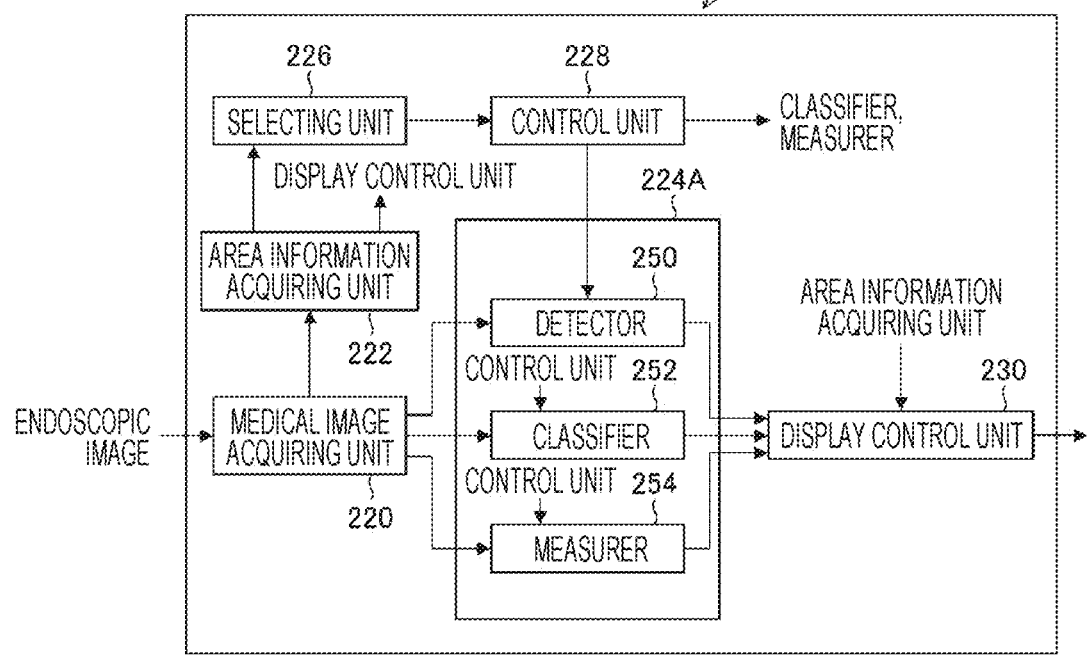
FIG. 18 is another diagram illustrating a state of controlling a recognizer.

FIG. 17 is a diagram illustrating an example of control of a recognizer. In this example, the control unit 228 causes only a specific recognizer to operate in accordance with an area, and the display control unit 230 causes a recognition result obtained by the operated recognizer to be displayed in a mode suitable for the area. In the case of performing detection, the control unit 228 causes the detector for esophagus 240 (the first detector for esophagus 240A for an upper portion or the second detector for esophagus 240B for a lower portion) to operate in a case where the area information indicates the esophagus, and causes the detector for stomach 241 (the first detector for stomach 241A for an upper portion or the second detector for stomach 241B for a lower portion) to operate in a case where the area information indicates the stomach. The classifier 252 or the measurer 254 may be operated in accordance with the purpose or the like of observation or diagnosis. An endoscopic image is input from the medical image acquiring unit 220 to the recognizer, and area information is input from the area information acquiring unit 222 to the display control unit 230. FIG. 18 is a diagram illustrating another example of control of a recognizer. In this example, the control unit 228 causes a plurality of recognizers (in this case, the detector 250, the classifier 252, and the measurer 254) to operate in parallel, and the display control unit 230 switches display of a recognition result in accordance with an area (for example, in the case of performing detection, a recognition result obtained by the detector 250 is displayed).

Display of Recognition Result and so Forth

In the second embodiment, display of an endoscopic image, a recognition result, and area information can be performed in a manner similar to that in the first embodiment (see FIGS. 8A to 11B).

As described above, the endoscope system according to the second embodiment is capable of displaying a recognition result of a medical image in a manner suitable for an area, like the endoscope system 10 according to the first embodiment. In addition, a user is capable of easily grasping switching of an area as a target to be recognized.

Application Example of Endoscope for Large Intestine

In the first and second embodiments, a description has been given mainly of the case of performing recognition and display for the esophagus or the stomach, which is an upper alimentary canal. However, the medical image processing apparatus and the medical image processing method according to the present invention can also be applied to the case of performing recognition and display for a lower alimentary canal, such as the rectum or the large intestine. In this case, a single recognizer may be provided, or a plurality of recognizers that are different in the type of recognition (detection, classification, measurement, or the like) or recognition area may be provided as in the above-described first and second embodiments. In the case of providing a plurality of recognizers that are different in recognition area, recognizers corresponding to, for example, the rectum, the sigmoid colon, the descending colon, the transverse colon, the ascending colon, the caecum, the ileum, and the jejunum can be provided. Preferably, each of these recognizers is a learned model that has learned by using an image set constituted by captured images of the area and performs processing of backpropagation.

Figure 19A:
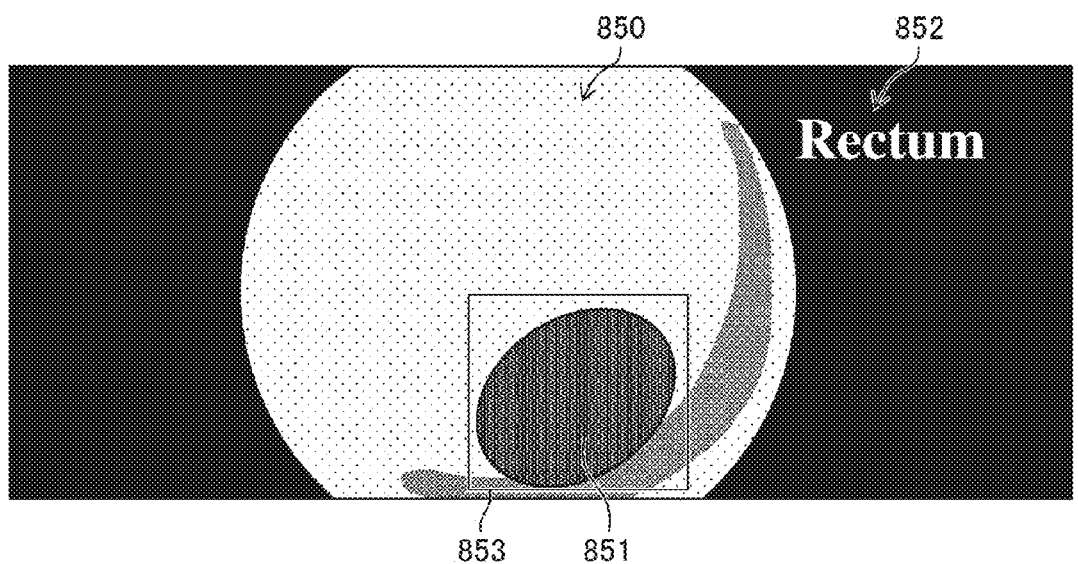
FIGS. 19A and 19B are diagrams illustrating display examples in an endoscope for large intestine.
Figure 19B:
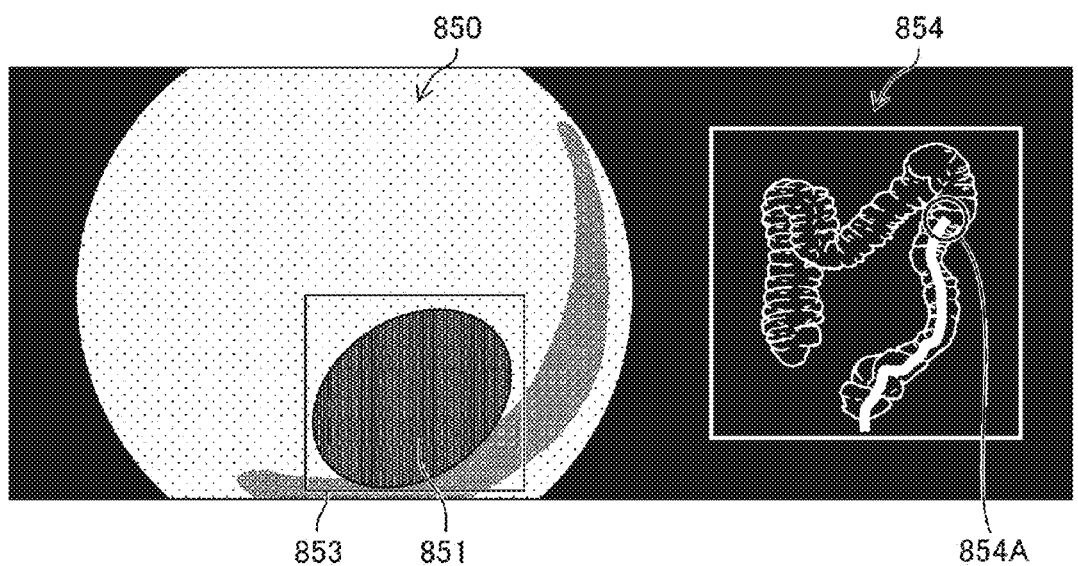

FIGS. 19A and 19B are diagrams illustrating display examples of an endoscopic image 850, and correspond to FIGS. 11A and 11B illustrating display examples of an upper alimentary canal. In each of FIGS. 19A and 19B, a frame 853 enclosing a region of interest 851 is displayed. FIG. 19A illustrates an example in which area information 852 is displayed by using a text ("Rectum") corresponding to the area. FIG. 19B illustrates an example in which area information is displayed in a schematic diagram 854 (a circle 854A is displayed at the position indicated by area information). Alternatively, display of the endoscopic image and the recognition result can be performed in a manner similar to that in the first and second embodiments (see FIGS. 8A to 11B). In this way, also in the case of performing recognition and display for a lower alimentary canal, a recognition result of a medical image can be displayed in a manner suitable for the area by displaying the recognition result or the like in a mode suitable for the area. In addition, a user is capable of easily grasping switching of the area as a target to be recognized.

Application to Images Other Than Endoscopic Image

In the first and second embodiments and other application examples described above, a description has been given of the case of performing recognition by using an endoscopic image, which is an aspect of a medical image. The medical image processing apparatus and the medical image processing method according to the present invention can also be applied to the case of using a medical image other than an endoscopic image, such as an ultrasound image.

APPENDICES

In addition to the first and second embodiments and other application examples described above, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit acquires the analysis result of the medical image from a recording device in which the analysis result is recorded, and
the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein
the medical image is an inside-of-living-body image depicting an inside of a living body, and
the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein
the medical image is an inside-of-living-body image depicting an inside of a living body, and
the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein
a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and
the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including
a feature quantity image generating unit that generates a feature quantity image through computation based on at least one of a normal-light image or a special-light image, the normal-light image being acquired by radiating light in a white range or light in a plurality of wavelength ranges as the light in the white range, the special-light image being acquired by radiating light in a specific wavelength range, wherein
the medical image is the feature quantity image.

Appendix 19

An endoscope apparatus including:
the medical image processing apparatus according to any one of appendices 1 to 18; and an endoscope that acquires an image by radiating at least any one of light in a white wavelength range or light in a specific wavelength range.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

The embodiments of the present invention and other examples have been described above. The present invention is not limited to the above-described aspects and various modifications can be made without deviating from the spirit of the present invention.

REFERENCE SIGNS LIST 10 endoscope system
100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
138 AFE
141 air/water supply button
142 suction button
143 function button
144 imaging button
170 light guide
200 endoscope processor apparatus
202 image input controller
204 image processing unit
204A image processing unit
205 communication control unit
206 video output unit
207 recording unit
208 operation unit
209 audio processing unit
209A speaker
210 CPU
211 ROM
212 RAM
220 medical image acquiring unit
222 area information acquiring unit
224 recognizer
224A recognizer
225 recognizer
226 selecting unit
228 control unit
230 display control unit
232 area estimating unit
234 medical image processing unit
236 accepting unit
238 recording control unit
240 detector for esophagus
240A first detector for esophagus
240B second detector for esophagus
241 detector for stomach
241A first detector for stomach
241B second detector for stomach
242 classifier for esophagus
243 classifier for stomach
244 measurer for esophagus
245 measurer for stomach
250 detector
252 classifier
254 measurer
260 endoscopic image
262 processed endoscopic image
264 area information
266 recognition result
268 processing condition
300 light source apparatus
310 light source
310B blue light source
310G green light source
310R red light source
310V violet light source
330 diaphragm
340 condenser lens
350 light source control unit
400 monitor
562 CNN
562A input layer
562B intermediate layer
562C output layer
564 convolutional layer
565 pooling layer
566 fully connected layer
800 endoscopic image
802 region of interest
804 figure
806 arrow
808 frame
810 frame
820 endoscopic image
822 recognition result display image
830 endoscopic image
832 region of interest
834 frame
836 area information
840 endoscopic image
842 schematic diagram
842A arrow
850 endoscopic image
851 region of interest
852 area information
853 frame
854 schematic diagram
854A circle
$F_1$ filter
$F_2$ filter
$F_n$ filter
S100 to S170 individual steps of medical image processing method

What is claimed is:

1. An endoscope system comprising:
an endoscope configured to capture an image of a subject;
a light source having a plurality of light source modes; and
one or more processors configured to:
use a plurality of recognizers corresponding respectively to a plurality of target areas in a living body;
cause the light source to irradiate the subject with light in one of the light source modes;
select one of the recognizers according to one of the target areas and the one of the light source modes; and
cause a monitor to display a result of recognition of the one of the recognizers.

2. The endoscope system according to claim 1, wherein the processors are configured to, by analyzing the image captured through the endoscope, acquire target area information indicating the one of the target areas.

3. The endoscope system according to claim 2, wherein the processors are configured to cause the monitor to display the result of recognition of the one of the recognizers along with the target area information.

4. The endoscope system according to claim 2, wherein the processors are configured to cause the monitor to display the result of recognition of the one of the recognizers in a display mode according to the one of the target areas indicated with the target area information.

5. The endoscope system according to claim 1, wherein the processors are configured to:
in a case where the endoscope captures an image of a first one of the target areas, cause the monitor to display the result of recognition with respect to the image captured with a first one of the light source modes; and
in a case where the endoscope captures an image of a second one of the target areas different from the first one of the target areas, cause the monitor not to display the result of recognition with respect to the image captured with the first one of the light source modes.

6. The endoscope system according to claim 5, wherein:
the first one of the target areas is an esophagus; and
the second one of the target areas is a stomach.

7. The endoscope system according to claim 5, wherein the light source irradiates the subject with special light in the first one of the light source modes.

8. The endoscope system according to claim 1, wherein the processors are configured to:
in a case where the endoscope captures an image of a first one of the target areas, cause the monitor to display the result of recognition; and
in a case where the endoscope captures an image of a second one of the target areas different from the first one of the target areas, cause the monitor not to display the result of recognition.

9. The endoscope system according to claim 1, wherein the light source includes light-emitting diodes respectively emitting red light, green light, blue light and violet light.

10. The endoscope system according to claim 1, wherein the processors are configured to, for duration that the endoscope captures the image, select the one of the recognizers independently of a user's operation.

11. The endoscope system according to claim 1, wherein the recognizers are a plurality of learned models having learned by using image sets constituted of captured images of different areas in a living body in accordance with target areas to be recognized.

12. The endoscope system according to claim 1, wherein the processors are configured to:
activate only one of the recognizers according to the one of the target areas; and
cause the monitor to display the result of recognition of the only one of the recognizers.

13. The endoscope system according to claim 1, wherein the processors are configured to:
activate two or more of the recognizers simultaneously; and
cause the monitor to display the result of recognition of one of the two or more of the recognizers selectively according to the one of the target areas.

14. The endoscope system according to claim 1, wherein the one of the recognizers performs, according to the one of the target areas, at least one of:
detection of a region of interest in the image;
classification on the image; and
measurement on the image.

15. The endoscope system according to claim 1, wherein the one of the recognizers performs, according to the one of the target areas, classification of a lesion on the image into at least two categories.

16. An operation method of an endoscope system comprising: an endoscope configured to capture an image of a subject; a light source having a plurality of light source modes; and one or more processors, the method comprising:
using a plurality of recognizers corresponding respectively to a plurality of target areas in a living body;
causing the light source to irradiate the subject with light in one of the light source modes;
selecting one of the recognizers according to one of the target areas and the one of the light source modes; and
causing a monitor to display a result of recognition of the one of the recognizers.

* * * * *